US006210883B1

(12) United States Patent
Reed et al.

(10) Patent No.: US 6,210,883 B1
(45) Date of Patent: Apr. 3, 2001

(54) COMPOUNDS AND METHODS FOR DIAGNOSIS OF LUNG CANCER

(75) Inventors: Steven G. Reed, Bellevue; Tong Tong Wang, Medina, both of WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/040,984

(22) Filed: Mar. 18, 1998

(51) Int. Cl.[7] ............................... C12Q 1/68; C07H 21/02; C07H 21/04; C12P 19/34
(52) U.S. Cl. ........................ 435/6; 435/91.2; 435/91.21; 435/810.1; 536/24.33; 536/24.3; 536/23.1
(58) Field of Search ........................... 435/6, 91.2, 91.21, 435/810.1; 536/23.5, 24.32, 24.33

(56) References Cited

U.S. PATENT DOCUMENTS 4,683,195 * 7/1987 Mullis et al. ............................ 435/6

OTHER PUBLICATIONS

Waldegger, et al. Cloning and characterization of a putative human serine/threonine protein kinase transcriptionally modified during anisotonic and isotonic alterations of cell volume. Proc. Natl. Acad. Sci. USA vol. 94, pp. 4440–4445, May 1997.*

GenEmbl database accession No. Y10032, May 1997.*

Hara et al., "Characterization of cell phenotype by a novel cDNA library subtraction system: expression of CD8α in a mast cell–derived interleukin–4–dependant cell line," *Blood* 84(1):189–199, Jul. 1, 1994.

* cited by examiner

*Primary Examiner*—Stephanie W. Zitomer
*Assistant Examiner*—Cynthia B. Wilder
(74) *Attorney, Agent, or Firm*—Seed Intellectual Property Law Group PLLC

(57) ABSTRACT

Compounds and methods for treating lung cancer are provided. The inventive compounds include polypeptides containing at least a portion of a lung tumor protein. Vaccines and pharmaceutical compositions for immunotherapy of lung cancer comprising such polypeptides, or DNA molecules encoding such polypeptides, are also provided, together with DNA molecules for preparing the inventive polypeptides.

10 Claims, No Drawings

COMPOUNDS AND METHODS FOR DIAGNOSIS OF LUNG CANCER

TECHNICAL FIELD

The present invention relates generally to compositions and methods for the treatment of lung cancer. The invention is more specifically related to nucleotide sequences that are preferentially expressed in lung tumor tissue, together with polypeptides encoded by such nucleotide sequences. The inventive nucleotide sequences and polypeptides may be used in vaccines and pharmaceutical compositions for the treatment of lung cancer.

BACKGROUND OF THE INVENTION

Lung cancer is the primary cause of cancer death among both men and women in the U.S., with an estimated 172,000 new cases being reported in 1994. The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Accordingly, there remains a need in the art for improved vaccines, treatment methods and diagnostic techniques for lung cancer.

SUMMARY OF THE INVENTION

The present invention provides methods for immunodiagnosis of lung cancer, together with kits for use in such methods. Polypeptides are disclosed which comprise at least an immunogenic portion of a lung tumor protein or a variant of said protein that differs only in conservative substitutions and/or modifications, wherein the lung tumor protein comprises an amino acid sequence encoded by a DNA molecule having a sequence selected from the group consisting of nucleotide sequences recited in SEQ ID NO: 1–86 and variants thereof. Such polypeptides may be usefully employed in the diagnosis and monitoring of lung cancer.

In one specific aspect of the present invention, methods are provided for detecting lung cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of lung cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of lung cancer.

The present invention further provides methods for detecting lung cancer comprising: (a) obtaining a biological sample from a patient; (b) contacting the sample with a first and a second oligonucleotide primer in a polymerase chain reaction, at least one of the oligonucleotide primers being specific for a DNA molecule that encodes one of the above polypeptides; and (c) detecting in the sample a DNA sequence that amplifies in the presence of the first and second oligonucleotide primers. In a preferred embodiment, at least one of the oligonucleotide primers comprises at least about 10 contiguous nucleotides of a DNA molecule including a sequence selected from the group consisting of SEQ ID NO: 1–86.

In a further aspect, the present invention provides a method for detecting lung cancer in a patient comprising: (a) obtaining a biological sample from the patient; (b) contacting the sample with an oligonucleotide probe specific for a DNA molecule that encodes one of the above polypeptides; and (c) detecting in the sample a DNA sequence that hybridizes to the oligonucleotide probe. Preferably, the oligonucleotide probe comprises at least about 15 contiguous nucleotides of a DNA molecule having a partial sequence selected from the group consisting of SEQ ID NO: 1–86.

In related aspects, diagnostic kits comprising the above oligonucleotide probes or primers are provided.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

As noted above, the present invention is generally directed to compositions and methods for the therapy of lung cancer. The compositions described herein include polypeptides, fusion proteins and DNA molecules. Also included within the present invention are molecules (such as an antibody or fragment thereof) that bind to the inventive polypeptides. Such molecules are referred to herein as "binding agents."

In one aspect, the subject invention discloses polypeptides comprising an immunogenic portion of a human lung tumor protein, wherein the lung tumor protein includes an amino acid sequence encoded by a DNA molecule including a sequence selected from the group consisting of (a) nucleotide sequences recited in SEQ ID NO: 1–86, (b) the complements of said nucleotide sequences, and (c) variants of such sequences. As used herein, the term "polypeptide" encompasses amino acid chains of any length, including full length proteins, wherein the amino acid residues are linked by covalent peptide bonds. Thus, a polypeptide comprising a portion of one of the above lung tumor proteins may consist entirely of the portion, or the portion may be present within a larger polypeptide that contains additional sequences. The additional sequences may be derived from the native protein or may be heterologous, and such sequences may (but need not) be immunoreactive and/or antigenic. As detailed below, such polypeptides may be isolated from lung tumor tissue or prepared by synthetic or recombinant means.

As used herein, an "immunogenic portion" of a lung tumor protein is a portion that is capable of eliciting an immune response in a patient inflicted with lung cancer and as such binds to antibodies present within sera from a lung cancer patient. Immunogenic portions of the proteins described herein may thus be identified in antibody binding assays. Such assays may generally be performed using any of a variety of means known to those of ordinary skill in the art, as described, for example, in Harlow and Lane, *Antibodies: A Laboratory Manual,* Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of lung cancer patients.

The compositions and methods of the present invention also encompass variants of the above polypeptides and DNA molecules. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. The identity of polypeptides may be determined by comparing sequences using computer algorithms well known to those of skill in the art, such as Megalign.

For lung tumor polypeptides with immunoreactive properties, variants may, alternatively, be identified by modifying the amino acid sequence of one of the above polypeptides, and evaluating the immunoreactivity of the modified polypeptide. For lung tumor polypeptides useful for the generation of diagnostic binding agents, a variant may be identified by evaluating a modified polypeptide for the ability to generate antibodies that detect the presence or absence of lung cancer. Such modified sequences may be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants of the inventive polypeptides may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA,* 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity to the recited sequence. The identity of nucleotide sequences may be determined by comparing sequences using computer algorithms well known to those of skill in the art, such as Megalign. Such variant nucleotide sequences will generally hybridize to the recite nucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The lung tumor polypeptides of the present invention, and DNA molecules encoding such polypeptides, may be isolated from lung tumor tissue using any of a variety of methods well known in the art. For example, DNA sequences corresponding to a gene (or a portion thereof) encoding one of the inventive lung tumor proteins may be isolated from a lung tumor cDNA library using a subtraction technique as described in detail below. Examples of such DNA sequences are provided in SEQ ID NO: 1–86. Partial DNA sequences thus obtained may be used to design oligonucleotide primers for the amplification of full-length DNA sequences from a human genomic DNA library or from a lung tumor cDNA library in a polymerase chain reaction (PCR), using techniques well known in the art (see, for example, Mullis et al., *Cold Spring Harbor Symp. Quant. Biol.* 51:263, 1987; Erlich ed., *PCR Technology,* Stockton Press, NY, 1989). For this approach, sequence-specific primers may be designed based on the nucleotide sequences provided herein and may be purchased or synthesized.

Once a DNA sequence encoding a polypeptide is obtained, the polypeptide may be produced recombinantly by inserting the DNA sequence into an expression vector and expressing the polypeptide in an appropriate host. Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes the recombinant polypeptide. Suitable host cells include prokaryotes, yeast, insect and higher eukaryotic cells. Preferably, the host cells employed are *E. coli,* yeast or a mammalian cell line, such as COS or CHO cells. The DNA sequences expressed in this manner may encode naturally occurring polypeptides, portions of naturally occurring polypeptides, or other variants thereof. Supernatants from suitable host/vector systems which secrete the recombinant polypeptide may first be concentrated using a commercially available filter. The concentrate may then be applied to a suitable purification matrix, such as an affinity matrix or ion exchange resin. Finally, one or more reverse phase HPLC steps can be employed to further purify the recombinant polypeptide.

The lung tumor polypeptides disclosed herein may also be generated by synthetic means. In particular, synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

In general, regardless of the method of preparation, the polypeptides disclosed herein are prepared in substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known lung tumor antigen, together with variants of such fusion proteins. The fusion proteins of the present invention may (but need not) include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

Polypeptides of the present invention that comprise an immunogenic portion of a lung tumor protein may generally be used for therapy of lung cancer, wherein the polypeptide stimulates the patient's own immune response to lung tumor cells. The present invention thus provides methods for using one or more of the compounds described herein (which may be polypeptides, DNA molecules or fusion proteins) for immunotherapy of lung cancer in a patient. As used herein, a "patient" refers to any warm-blooded animal, preferably a human. A patient may be afflicted with disease, or may be free of detectable disease. Accordingly, the compounds disclosed herein may be used to treat lung cancer or to inhibit the development of lung cancer. The compounds may be administered either prior to or following surgical removal of primary tumors and/or treatment by administration of radiotherapy and conventional chemotherapeutic drugs.

In these aspects, the inventive polypeptide is generally present within a pharmaceutical composition or a vaccine. Pharmaceutical compositions may comprise one or more polypeptides, each of which may contain one or more of the above sequences (or variants thereof), and a physiologically acceptable carrier. The vaccines may comprise one or more such polypeptides and an immune-response enhancer, such as an adjuvant, biodegradable microsphere (e.g., polylactic galactide) or a liposome (into which the polypeptide is incorporated). Pharmaceutical compositions and vaccines may also contain other epitopes of lung tumor antigens, either incorporated into a fusion protein as described above (i.e., a single polypeptide that contains multiple epitopes) or present within a separate polypeptide.

Alternatively, a pharmaceutical composition or vaccine may contain DNA encoding one or more of the above polypeptides and/or fusion proteins, such that the polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guerrin) that expresses an epitope of a lung cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in published PCT application WO 90/11092, and Ulmer et al., *Science* 259:1745–1749, 1993, reviewed by Cohen, *Science*

259:1691–1692, 1993. The uptake of naked DNA may be increased by coating the DNA onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against lung tumor cells in a treated patient. A suitable immune response is at least 10–50% above the basal (i.e., untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of immune-response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in ex vivo treatment of lung cancer. For example, cells of the immune system, such as T cells, may be isolated from the peripheral blood of a patient, using a commercially available cell separation system, such as CellPro Incorporated's (Bothell, Wash.) CEPRATE™ system (see U.S. Pat. Nos. 5,240,856; 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

Polypeptides and fusion proteins of the present invention may also, or alternatively, be used to generate binding agents, such as antibodies or fragments thereof, that are capable of detecting metastatic human lung tumors. Binding agents of the present invention may generally be prepared using methods known to those of ordinary skill in the art, including the representative procedures described herein. Binding agents are capable of differentiating between patients with and without lung cancer, using the representative assays described herein. In other words, antibodies or other binding agents raised against a lung tumor protein, or a suitable portion thereof, will generate a signal indicating the presence of primary or metastatic lung cancer in at least about 20% of patients afflicted with the disease, and will generate a negative signal indicating the absence of the disease in at least about 90% of individuals without primary or metastatic lung cancer. Suitable portions of such lung tumor proteins are portions that are able to generate a binding agent that indicates the presence of primary or metastatic lung cancer in substantially all (i.e., at least about 80%, and preferably at least about 90%) of the patients for which lung cancer would be indicated using the full length protein, and that indicate the absence of lung cancer in substantially all of those samples that would be negative when tested with full length protein. The representative assays described below, such as the two-antibody sandwich assay, may generally be employed for evaluating the ability of a binding agent to detect metastatic human lung tumors.

The ability of a polypeptide prepared as described herein to generate antibodies capable of detecting primary or metastatic human lung tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic lung cancer for the presence of a polypeptide that binds to the generated antibodies. Such test assays may be performed, for example, using a representative procedure described below. Polypeptides that generate antibodies capable of detecting at least 20% of primary or metastatic lung tumors by such procedures are considered to be useful in assays for detecting primary or metastatic human lung tumors. Polypeptide specific antibodies may be used alone or in combination to improve sensitivity.

Polypeptides capable of detecting primary or metastatic human lung tumors may be used as markers for diagnosing lung cancer or for monitoring disease progression in patients. In one embodiment, lung cancer in a patient may be diagnosed by evaluating a biological sample obtained from the patient for the level of one or more of the above polypeptides, relative to a predetermined cut-off value. As used herein, suitable "biological samples" include blood, sera, urine and/or lung secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations.

In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual,* Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of lung cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without lung cancer. In general, a sample generating a signal that is three standard deviations above the predetermined cut-off value is considered positive for lung cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for lung cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of lung cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 µg, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of lung cancer. In this embodiment, assays as described above for the diagnosis of lung cancer may be performed over time, and the change in the level of reactive polypeptide(s) evaluated. For example, the assays may be performed every 24–72 hours for a period of 6 months to 1 year, and thereafter performed as needed. In general, lung cancer is progressing in those patients in whom the level of polypeptide detected by the binding agent increases over time. In contrast, lung cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual,* Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate lung tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g. U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify lung tumor-specific cDNA derived from a biological sample, wherein at least one of the oligonucleotide primers is specific for a DNA molecule encoding a lung tumor protein of the present invention. The presence of the amplified cDNA is then detected using techniques well known in the art, such as gel electrophoresis. Similarly, oligonucleotide probes specific for a DNA molecule encoding a lung tumor protein of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule comprising sequence selected from SEQ ID NO: 1–86. Preferably, oligonucleotide probes for use in the inventive diagnostic methods comprise at least about 15 contiguous oligonucleotides of a DNA molecule comprising a sequence provided in SEQ ID NO: 1–86. Techniques for both PCR based assays and hybridization assays are well known in the art (see, for example, Mullis et al. Ibid; Ehrlich, Ibid). Primers or probes may thus be used to detect lung tumor-specific sequences in biological samples, including blood, semen, lung tissue and/or lung tumor tissue.

The following Examples are offered by way of illustration and not by way of limitation.

EXAMPLES

Example 1

Isolation and Characterization of cDNA Sequences Encoding Lung Tumor Polypeptides This example illustrates the isolation of cDNA molecules encoding lung tumor-specific polypeptides from lung tumor cDNA libraries.

A. Isolation of cDNA Sequences from a Lung Squamous Cell Carcinoma Library

A human lung squamous cell carcinoma cDNA expression library was constructed from poly $A^+$ RNA from a pool of two patient tissues using a Superscript Plasmid System for cDNA Synthesis and Plasmid Cloning kit (BRL Life Technologies, Gaithersburg, Md.) following the manufacturer's protocol. Specifically, lung carcinoma tissues were homogenized with polytron (Kinematica, Switzerland) and total RNA was extracted using Trizol reagent (BRL Life Technologies) as directed by the manufacturer. The poly $A^+$ RNA was then purified using an oligo dT cellulose column as described in Sambrook et al., *Molecular Cloning: A Laboratory Manual,* Cold Spring Harbor Laboratories, Cold Spring Harbor, N.Y., 1989. First-strand cDNA was synthesized using the NotI/Oligo-dT18 primer. Double-stranded cDNA was synthesized, ligated with BstXI/EcoRI adaptors (Invitrogen, San Diego, Calif.) and digested with NotI. Following size fractionation with cDNA size fractionation columns (BRL Life Technologies), the cDNA was ligated into the BstXI/NotI site of pcDNA3.1 (Invitrogen) and transformed into ElectroMax *E. coli* DH10B cells (BRL Life Technologies) by electroporation.

Using the same procedure, a normal human lung cDNA expression library was prepared from a pool of four tissue specimens. The cDNA libraries were characterized by determining the number of independent colonies, the percentage of clones that carried insert, the average insert size and by sequence analysis. The lung squamous cell carcinoma library contained $2.7 \times 10^6$ independent colonies, with 100% of clones having an insert and the average insert size being 2100 base pairs. The normal lung cDNA library contained $1.4 \times 10^6$ independent colonies, with 90% of clones having inserts and the average insert size being 1800 base pairs. For both libraries, sequence analysis showed that the majority of clones had a full length cDNA sequence and were synthesized from mRNA.

cDNA library subtraction was performed using the above lung squamous cell carcinoma and normal lung cDNA libraries, as described by Hara et al. (*Blood,* 84:189–199, 1994) with some modifications. Specifically, a lung squamous cell carcinoma-specific subtracted cDNA library was generated as follows. Normal tissue cDNA library (80 $\mu$g) was digested with BamHI and XhoI, followed by a filling-in reaction with DNA polymerase Klenow fragment. After phenol-chloroform extraction and ethanol precipitation, the DNA was dissolved in 133 $\mu$l of $H_2O$, heat-denatured and mixed with 133 $\mu$l (133 $\mu$g) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (67 $\mu$l) was added and the biotinylation reaction was repeated. After extraction with butanol five times, the DNA was ethanol-precipitated and dissolved in 23 $\mu$l $H_2O$ to form the driver DNA.

To form the tracer DNA, 10 $\mu$g lung squamous cell carcinoma cDNA library was digested with NotI and SpeI, phenol chloroform extracted and passed through Chroma spin-400 columns (Clontech). Typically, 5 $\mu$g of cDNA was recovered after the sizing column. Following ethanol precipitation, the tracer DNA was dissolved in 5 $\mu$l $H_2O$. Tracer DNA was mixed with 15 $\mu$l driver DNA and 20 $\mu$l of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 $\mu$l $H_2O$, mixed with 8 $\mu$l driver DNA and 20 $\mu$l of 2×hybridization buffer, and subjected to a hybridization at 68° C. for 2 hours (short hybridization [SH]). After removal of biotinylated double-stranded DNA, subtracted cDNA was ligated into NotI/SpeI site of chloramphenicol resistant pBCSK$^+$ (Stratagene, La Jolla, Calif.) and transformed into ElectroMax *E. coli* DH10B cells by electroporation to generate a lung squamous cell carcinoma specific subtracted cDNA library (herein after referred to as "lung subtraction I").

A second lung squamous cell carcinoma specific subtracted cDNA library (referred to as "lung subtraction II") was generated in a similar way to the lung subtraction library I, except that eight frequently recovered genes from lung subtraction I were included in the driver DNA, and 24,000 independent clones were recovered.

To analyze the subtracted cDNA libraries, plasmid DNA was prepared from 320 independent clones, randomly picked from the subtracted lung squamous cell carcinoma specific libraries. Representative cDNA clones were further characterized by DNA sequencing with a Perkin Elmer/Applied Biosystems Division Automated Sequencer Model 373A and/or Model 377 (Foster City, Calif.). The cDNA sequences for sixty isolated clones are provided in SEQ ID NO: 1–60. These sequences were compared to known sequences in the gene bank using the EMBL and GenBank databases (release 96). No significant homologies were found to the sequences provided in SEQ ID NO: 2, 3, 19, 38 and 46. The sequences of SEQ ID NO: 1, 6–8, 10–13, 15, 17, 18, 20–27, 29, 30, 32, 34–37, 39–45, 47–49, 51, 52, 54, 55 and 57–59 were found to show some homology to previously identified expressed sequence tags (ESTs). The sequences of SEQ ID NO: 9, 28, 31 and 33 were found to show some homology to previously identified non-human gene sequences and the sequences of SEQ ID NO: 4, 5, 14, 50, 53, 56 and 60 were found to show some homology to gene sequences previously identified in humans.

The subtraction procedure described above was repeated using the above lung squamous cell carcinoma cDNA library as the tracer DNA, and the above normal lung tissue cDNA library and a cDNA library from normal liver and heart (constructed from a pool of one sample of each tissue as described above), plus twenty other cDNA clones that were frequently recovered in lung subtractions I and II, as the driver DNA. The normal liver and heart cDNA library contained $1.76 \times 10^6$ independent colonies, with 100% of clones having inserts and the average insert size being 1600 base pairs. Ten additional clones were isolated (SEQ ID NO: 61–70). Comparison of these cDNA sequences with those in the gene bank as described above, revealed no significant homologies to the sequences provided in SEQ ID NO: 62 and 67. The sequences of SEQ ID NO: 61, 63–66, 68 and 69 were found to show some homology to previously isolated ESTs and the sequence provided in SEQ ID NO: 70 was found to show some homology to a previously identified rat gene.

B. Isolation of cDNA Sequences from a Lung Adenocarcinoma Library

A human lung adenocarcinoma cDNA expression library was constructed as described above. The library contained $3.2 \times 10^6$ independent colonies, with 100% of clones having an insert and the average insert size being 1500 base pairs. Library subtraction was performed as described above using the normal lung and normal liver and heart cDNA expression libraries described above as the driver DNA. Twenty-six hundred independent clones were recovered.

Initial cDNA sequence analysis from 100 independent clones revealed many ribosomal protein genes. The cDNA sequences for fifteen clones isolated in this subtraction are provided in SEQ ID NO: 71–86. Comparison of these sequences with those in the gene bank as described above revealed no significant homologies to the sequence provided in SEQ ID NO: 84. The sequences of SEQ ID NO: 71, 73, 74, 77, 78 and 80–82 were found to show some homology to previously isolated ESTs, and the sequences of SEQ ID NO: 72, 75, 76, 79, 83 and 85 were found to show some homology to previously identified human genes.

Example 2

Determination of Tissue Specificity of Lung Tumor Polypeptides

Using gene specific primers, mRNA expression levels for seven representative lung tumor polypeptides described in Example 1 were examined in a variety of normal and tumor tissues using RT-PCR.

Briefly, total RNA was extracted from a variety of normal and tumor tissues using Trizol reagent as described above. First strand synthesis was carried out using 2 µg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. 1 µl of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous cell carcinoma from 3 patients, lung adenocarcinoma, colon tumor from 2 patients, breast tumor and prostate tumor), and thirteen different normal tissues (lung from 4 donors, prostate, brain, kidney, liver, ovary, skeletal muscle, skin, small intestine, stomach, myocardium, retina and testes). Using a 10-fold amount of cDNA, the antigen LST-S-1-90 (SEQ ID NO: 3) was found to be expressed at high levels in lung squamous cell carcinoma and in breast tumor, and at low to undetectable levels in the other tissues examined.

The antigen LST-S2-68 (SEQ ID NO: 15) appears to be specific to lung and breast tumor, however, expression was also detected in normal kidney. Antigens LST-S1-169 (SEQ ID NO: 6) and LST-S1-133 (SEQ ID NO: 5) appear to be very abundant in lung tissues (both normal and tumor), with the expression of these two genes being decreased in most of the normal tissues tested. Both LST-S1-169 and LST-S1-133 were also expressed in breast and colon tumors. Antigens LST-S1-6 (SEQ ID NO: 7) and LST-S2-I2-5F (SEQ ID NO: 47) did not show tumor or tissue specific expression, with the expression of LST-S1-28 being rare and only detectable in a few tissues. The antigen LST-S3-7 (SEQ ID NO: 63) showed lung and breast tumor specific expression, with its message only being detected in normal testes when the PCR was performed for 30 cycles. Lower level expression was detected in some normal tissues when the cycle number was increased to 35. Antigen LST-S3-13 (SEQ ID NO: 66) was found to be expressed in 3 out of 4 lung tumors, one breast tumor and both colon tumor samples. Its expression in normal tissues was lower compared to tumors, and was only detected in 1 out of 4 normal lung tissues and in normal tissues from kidney, ovary and retina. Expression of antigens LST-S3-4 (SEQ ID NO: 62) and LST-S3-14 (SEQ ID NO: 67) was rare and did not show any tissue or tumor specificity. Consistent with Northern blot analyses, the RT-PCT results on antigen LAT-S1-A-10A (SEQ ID NO: 78) suggested that its expression is high in lung, colon, stomach and small intestine tissues, including lung and colon tumors, whereas its expression was low or undetectable in other tissues.

Example 4

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. A method for detecting the presence of lung cancer in a patient comprising:
   (a) obtaining a biological sample from the patient;
   (b) contacting the biological sample with at least two oligonucleotide primers in a polymerase chain reaction, wherein at least one of the oligonucleotides hybridizes to a DNA molecule having a sequence selected from the group consisting of nucleotide sequences recited in SEQ ID NOS: 1, 2, 3, 5, 6, 10, 14, 15, 18 and 40, the complements of said nucleotide sequences; and
   (c) detecting in the biological sample a DNA sequence that amplifies in the presence of the oligonucleotide primers, thereby detecting presence of lung cancer.

2. The method of claim 1, wherein at least one of the oligonucleotide primers comprises at least about 10 contiguous nucleotides of a DNA molecule having a sequence selected from SEQ ID NOS: 1, 2, 3, 5, 6, 10, 14, 15, 18 and 40.

3. A diagnostic kit comprising at least two oligonucleotide primers, at least one of the oligonucleotide primers hybridizes to a DNA molecule having a sequence selected from the group consisting of nucleotide sequences recited in SEQ ID NOS: 1, 2, 3, 5, 6, 10, 14, 15, 18 and 40, the complements of said nucleotide sequences and sequences that hybridize to said nucleotide sequences under stringent conditions.

4. A diagnostic kit of claim 3 wherein at least one of the oligonucleotide primers comprises at least about 10 contiguous nucleotides of a DNA molecule having a sequence selected from SEQ ID NOS: 1, 2, 3, 5, 6, 10, 14, 15, 18 and 40.

5. A method for detecting the presence of lung cancer in a patient, comprising:
   (a) obtaining a biological sample from the patient;
   (b) contacting the biological sample with an oligonucleotide probe specific for a DNA molecule having a sequence selected from the group consisting of nucleotide sequences recited in SEQ ID NOS: 1, 2, 3, 5, 6, 10, 14, 15, 18, and 40, the complements of said nucleotide sequences, and sequences that hybridize to said nucleotide sequences under stringent conditions; and (c) detecting in the biological sample a DNA sequence that hybridizes to the oligonucleotide probe, thereby detecting presence of lung cancer in the patient.

6. The method of claim 5 wherein the oligonucleotide probe comprises at least about 15 contiguous nucleotides of a DNA molecule having a sequence selected from the group consisting of SEQ ID NOS: 1, 2, 3, 5, 6, 10, 14, 15, 18 and 40.

7. A diagnostic kit comprising an oligonucleotide probe specific for a DNA molecule having a sequence selected from the group consisting of: nucleotide sequences recited in SEQ ID NOS: 1, 2, 3, 5, 6, 10, 14, 15, 18 and 40; the complements of said nucleotide sequences; and sequences that hybridize to said nucleotide sequences under stringent conditions.

8. The diagnostic kit of claim 7, wherein the oligonucleotide probe comprises at least about 15 contiguous nucleotides of a DNA molecule having a sequence selected from the group consisting of SEQ ID NOS: 1, 2, 3, 5, 6, 10, 14, 15, 18 and 40.

9. A method for detecting the presence of lung cancer in a patient comprising:
   (a) obtaining a biological sample from the patient;
   (b) contacting the biological sample with at least two oligonucleotide primers in a polymerase chain reaction, wherein at least one of the oligonucleotides hybridizes to a DNA consisting of the nucleotide sequence recited in SEQ ID NO: 5 and the complement of said nucleotide sequence; and
   (c) detecting in the biological sample a DNA sequence that amplifies in the presence of the oligonucleotide primers, thereby detecting the presence of lung cancer.

10. A diagnostic kit comprising at least two oligonucleotide primers, at least one of the oligonucleotide primers hybridizes to a DNA consisting of the nucleotide sequence recited in SEQ ID NO: 5, the complement of said nucleotide sequence; and sequences that hybridizes to said nucleotide sequence under stringent conditions.

\* \* \* \* \*

SEQUENCE LISTING (1) GENERAL INFORMATION:

(iii) NUMBER OF SEQUENCES: 86

(2) INFORMATION FOR SEQ ID NO: 1:

(i) SEQUENCE CHARACTERISTICS:
      (A) LENGTH: 315 base pairs
      (B) TYPE: nucleic acid (C) STRANDEDNESS: single
        (D) TOPOLOGY: linear (xi) SEQUENCE DESCRIPTION: SEQ ID NO: 1:

GCAGAGACAG ACTGGTGGTT GAACCTGGAG GTGCCAAAAA AGCCAGCTGC GGGCCCAGGA    60

CAGCTGCCGT GAGACTCCCG ATGTCACAGG CAGTCTGTGT GGTTACAGCG CCCCTCAGTG   120

TTCATCTCCA GCAGAGACAA CGGAGGAGGC TCCCACCAGG ACGGTTCTCA TTATTTATAT   180

GTTAATATGT TTGTAAACTC ATGTACAGTT TTTTTTGGGG GGGAAGCAAT GGGAANGGTA   240

NAAATTACAA ATAGAATCAT TTGCTGTAAT CCTTAAATGG CAAACGGTCA GGCCACGTGA   300

AAAAAAAAAA AAAAA                                                  315

(2) INFORMATION FOR SEQ ID NO: 2:

(i) SEQUENCE CHARACTERISTICS:
        (A) LENGTH: 380 base pairs
        (B) TYPE: nucleic acid
        (C) STRANDEDNESS: single
        (D) TOPOLOGY: linear (xi) SEQUENCE DESCRIPTION: SEQ ID NO: 2:

ATTTAGGCTT AAGATTTTGT TTACCCTTGT TACTAAGGAG CAAATTAGTA TTAAAGTATA    60

ATATATATAA ACAAATACAA AAAGTTTTGA GTGGTTCAGC TTTTTTATTT TTTTTAATGG   120

CATAACTTTT AACAACACTG CTCTGTAATG GGTTGAACTG TGGTACTCAG ACTGAGATAA   180

CTGAAATGAG TGGATGTATA GTGTTATTGC ATAATTATCC CACTATGAAG CAAAGGGACT   240

GGATAAATTC CCAGTCTAGA TTATTAGCCT TTGTTAACCA TCAAGCACCT AGAAGAAGAA   300

TTATTGGAAA TTTTGTCCTC TGTAACTGGC ACTTTGGGGT GTGACTTATC TTTTGCCTTT   360

GTAAAAAAAA AAAAAAAAA                                              380

(2) INFORMATION FOR SEQ ID NO: 3:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (xi) SEQUENCE DESCRIPTION: SEQ ID NO: 3:

TTGTAAGTAT ACAATTTTAG AAAGGATTAA ATGTTATTGA TCATTTTACT GAATACTGCA    60

CATCCTCACC ATACACCATC CACTTTCCAA TAACATTTAA TCCTTTCTAA AATTGTAAGT   120

ATACAATTGT ACTTTCTTTG GATTTTCATA ACAAATATAC CATAGACTGT TAATTTTATT   180

GAAGTTTCCT TAATGGAATG AGTCATTTTT GTCTTGTGCT TTTGAGGTTA CCTTTGCTTT   240

GACTTCCAAC AATTTGATCA TATAGTGTTG AGCTGTGGAA ATCTTTAAGT TTATTCTATA   300

GCAATAATTT CTATTNNNAG ANNCCNGGNN NAAAANNANN ANNAAA                 346

(2) INFORMATION FOR SEQ ID NO: 4:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (xi) SEQUENCE DESCRIPTION: SEQ ID NO: 4:

ACTAGTCTCA TTACTCCAGA ATTATGCTCT TGTACCTGTG TGGCTGGGTT TCTTAGTCGT    60

TGGTTTGGTT TGGTTTTTTG AACTGGTATG TAGGGTGGTT CACAGTTCTA ATGTAAGCAC   120

| | |
|---|---:|
| TCTCTTCTCC AAGTTGTGCT TTGTGGGAC AATCATTCTT TGAACATTAG AGAGGAAGGC | 180 |
| AGTTCAAGCT GTTGAAAAGA CTATTGCTTA TTTTTGTTTT TAAAGACCTA CTTGACGTCA | 240 |
| TGTGGACAGT GCACGTGCCT TACGCTACAT CTTGTTTTCT AGGAAGAAGG GGATGCNGGG | 300 |
| AAGGANTGGG TGCTTTGTGA TGGATAAAAC GNCTAAATAA CACACCTTTA CATTTTGAAA | 360 |
| AAAACAAAAC AA | 372 |

(2) INFORMATION FOR SEQ ID NO: 5:

(i) SEQUENCE CHARACTERISTICS:
        (A) LENGTH: 698 base pairs
        (B) TYPE: nucleic acid
        (C) STRANDEDNESS: single
        (D) TOPOLOGY: linear (xi) SEQUENCE DESCRIPTION: SEQ ID NO: 5:

| | |
|---|---:|
| ACTAGTANGA TAGAAACACT GTGTCCCGAG AGTAAGGAGA GAAGCTACTA TTGATTAGAG | 60 |
| CCTAACCCAG GTTAACTGCA AGAAGAGGCG GGATACTTTC AGCTTTCCAT GTAACTGTAT | 120 |
| GCATAAAGCC AATGTAGTCC AGTTTCTAAG ATCATGTTCC AAGCTAACTG AATCCCACTT | 180 |
| CAATACACAC TCATGAACTC CTGATGGAAC AATAACAGGC CCAAGCCTGT GGTATGATGT | 240 |
| GCACACTTGC TAGACTCAGA AAAAATACTA CTCTCATAAA TGGGTGGGAG TATTTTGGGT | 300 |
| GACAACCTAC TTTGCTTGGC TGAGTGAAGG AATGATATTC ATATNTTCAT TTATTCCATG | 360 |
| GACATTTAGT TAGTGCTTTT TATATACCAG GCATGATGCT GAGTGACACT CTTGTGTATA | 420 |
| TNTCCAAATN TTNGTNCNGT CGCTGCACAT ATCTGAAATC CTATATTAAG ANTTTCCCAA | 480 |
| NATGANGTCC CTGGTTTTTC CACGCCACTT GATCNGTCAA NGATCTCACC TCTGTNTGTC | 540 |
| CTAAAACCNT CTNCTNNANG GTTAGACNGG ACCTCTCTTC TCCCTTCCCG AANAATNAAG | 600 |
| TGTGNGAAGA NANCCNCNCN CCCCCCTNCN TNCNNCCTNG CCNGCTNNNC CNCNTGTNGG | 660 |
| GGGNGCCGCC CCCGCGGGGG GACCCCCCCN TTTTCCCC | 698 |

(2) INFORMATION FOR SEQ ID NO: 6:

(i) SEQUENCE CHARACTERISTICS:
        (A) LENGTH: 740 base pairs
        (B) TYPE: nucleic acid
        (C) STRANDEDNESS: single
        (D) TOPOLOGY: linear
    (xi) SEQUENCE DESCRIPTION: SEQ ID NO: 6:

| | |
|---|---:|
| ACTAGTCAAA AATGCTAAAA TAATTTGGGA GAAAATATTT TTAAGTAGT GTTATAGTTT | 60 |
| CATGTTTATC TTTTATTATG TNTTGTGAAG TTGTGTCTTT TCACTAATTA CCTATACTAT | 120 |
| GCCAATATTT CCTTATATCT ATCCATAACA TTTATACTAC ATTTGTAAGA GAATATGCAC | 180 |
| GTGAAACTTA ACACTTTATA AGGTAAAAAT GAGGTTTCCA AGATTAATA ATCTGATCAA | 240 |
| GTTCTTGTTA TTTCCAAATA GAATGGACTT GGTCTGTTAA GGGGCTAAGG GAGAAGAAGA | 300 |
| AGATAAGGTT AAAAGTTGTT AATGACCAAA CATTCTAAAA GAAATGCAAA AAAAAATTTA | 360 |
| TTTTCAAGCC TTCGAACTAT TTAAGGAAAG CAAAATCATT TCCTANATGC ATATCATTTG | 420 |
| TGAGANTTTC TCANTAATAT CCTGAATCAT TCATTTCAGC TNAGGCTTCA TGTTGACTCG | 480 |
| ATATGTCATC TAGGGAAAGT CTATTTCATG GTCCAAACCT GTTGCCATAG TTGGTNAGGC | 540 |
| TTTCCTTTAA NTGTGAANTA TTNACANGAA ATTTTCTCTT TNANAGTTCT TNATAGGGTT | 600 |
| AGGGGTGTGG GAAAAGCTTC TAACAATCTG TAGTGTTNCG TGTTATCTGT NCAGAACCAN | 660 |
| AATNACGGAT CGNANGAAGG ACTGGGTCTA TTTACANGAA CGAATNATCT NGTTNNNTGT | 720 |

GTNNNCAACT CCNGGGAGCC                                              740

(2) INFORMATION FOR SEQ ID NO: 7:

(i) SEQUENCE CHARACTERISTICS:
        (A) LENGTH: 670 base pairs
        (B) TYPE: nucleic acid
        (C) STRANDEDNESS: single
        (D) TOPOLOGY: linear (xi) SEQUENCE DESCRIPTION: SEQ ID NO: 7:

GCTGGGGAGC TCGGCATGGC GGTCCCCGCT GCAGCCATGG GGCCCTCGGC GTTGGGCCAG    60

AGCGGCCCCG GCTCGATGGC CCCGTGGTGC TCAGTGAGCA GCGGCCCGTC GCGCTACGTG   120

CTTGGGATGC AGGAGCTGTT CCGGGGCCAC AGCAAGACCG CGAGTTCCTG GCGCACAGCG   180

CCAAGGTGCA CTCGGTGGCC TGGAGTTGCG ACGGGCGTCG CCTACCTCGG GGTCTTCGAC   240

AAGACGCCAC GTCTTCTTGC TGGANAANGA CCGTTGGTCA AGAAAACAA TTATCGGGGA    300

CATGGGGATA GTGTGGACCA CTTTGTTGGC ATCCAAGTAA TCCTGACCTA TTTGTTACGG   360

CGTCTGGAGA TAAAACCATT CGCATCTGGG ATGTGAGGAC TACAAAATGC ATTGCCACTG   420

TGAACACTAA AGGGGAGAAC ATTAATATCT GCTGGANTCC TGATGGGCAN ACCATTGCTG   480

TAGCNACAAG GATGATGTGG TGACTTTATT GATGCCAAGA AACCCCGTTC CAAAGCAAAA   540

AAACANTTCC AANTTCGAAG TCACCNAAAT CTCCTGGAAC AATGAACATN AATATNTTCT   600

TCCTGACAAT GGNCCTTGGG TGTNTCACAT CCTCAGCTNC CCCAAAACTG AANCCTGTNC   660

NATCCACCCC                                                         670

(2) INFORMATION FOR SEQ ID NO: 8:

(i) SEQUENCE CHARACTERISTICS:
        (A) LENGTH: 689 base pairs
        (B) TYPE: nucleic acid
        (C) STRANDEDNESS: single
        (D) TOPOLOGY: linear (xi) SEQUENCE DESCRIPTION: SEQ ID NO: 8:

ACTAGTATCT AGGAATGAAC AGTAAAAGAG GAGCAGTTGG CTACTTGATT ACAACAGAGT    60

AAATGAAGTA CTGGATTTGG GAAAACCTGG TTTTATTAGA ACATATGGAA TGAAAGCCTA   120

CACCTAGCAT TGCCTACTTA GCCCCCTGAA TTAACAGAGC CCAATTGAGA CAAACCCCTG   180

GCAACAGGAA ATTCAAGGGA GAAAAGTAA GCAACTTGGG CTAGGATGAG CTGACTCCCT    240

TAGAGCAAAG GANAGACAGC CCCCATTACC AAATACCATT TTTGCCTGGG GCTTGTGCAG   300

CTGGCAGTGT TCCTGCCCCA GCATGGCACC TTATNGTTTT GATAGCAACT TCGTTGAATT   360

TTCACCAACT TATTACTTGA AATTATAATA TAGCCTGTCC GTTTGCTGTN TCCAGGCTGT   420

GATATATNTT CCTAGTGGTT TGACTTTNAA AATAAATNAG GTTTANTTTT CTCCCCCCNN   480

CNNTNCTNCC NNTCNCTCNN CNNTCCCCCC CNCTCNGTCC TCCNNNNTTN GGGGGGGCCN   540

CCCCNCGGN GGACCCCCCT TTGGTCCCTT AGTGGAGGTT NATGGCCCCT GGNNTTATCC    600

NGGCCNTANN TTTCCCCGTN NNAAATGNTT CCCCCTCCCA NTCCCNCCAC CTCAANCCGG   660

AAGCCTAAGT TTNTACCCTG GGGGTCCCC                                    689

(2) INFORMATION FOR SEQ ID NO: 9:

(i) SEQUENCE CHARACTERISTICS:
        (A) LENGTH: 674 base pairs
        (B) TYPE: nucleic acid (C) STRANDEDNESS: single
(D) TOPOLOGY: linear (xi) SEQUENCE DESCRIPTION: SEQ ID NO: 9:

```
GTCCACTCTC CTTTGAGTGT ACTGTCTTAC TGTGCACTCT GTTTTTCAAC TTTCTAGATA      60
TAAAAAATGC TTGTTCTATA GTGGAGTAAG AGCTCACACA CCCAAGGCAG CAAGATAACT     120
GAAAAAAGCG AGGCTTTTTT GCCACCTTGG TAAAGGCCAG TTCACTGCTA TAGAACTGCT     180
ATAAGCCTGA AGGGAAGTAG CTATGAGACT TTCCATTTTT CTTAGTTCTC CCAATAGGCT     240
CCTTCATGGA AAAAGGCTTC CTGTAATAAT TTTCACCTAA TGAATTAGCA GTGTGATTAT     300
TTCTGAAATA AGAGACAAAT TGGGCCGCAG AGTCTTCCTG TGATTTAAAA TAAACAACCC     360
AAAGTTTTGT TTGGTCTTCA CCAAAGGACA TACTCTAGGG GGTATGTTGT TGAAGACATT     420
CAAAAACATT AGCTGTTCTG TCTTTCAATT TCAAGTTATT TTGGAGACTG CCTCCATGTG     480
AGTTAATTAC TTTGCTCTGG AACTAGCATT ATTGTCATTA TCATCACATT CTGTCATCAT     540
CATCTGAATA ATATTGTGGA TTTCCCCCTC TGCTTGCATC TTCTTTTGAC TCCTCTGGGA     600
ANAAATGTCA AAAAAAAGG TCGATCTACT CNGCAAGGNC CATCTAATCA CTGCGCTGGA     660
AGGACCCNCT GCCC                                                      674
```

(2) INFORMATION FOR SEQ ID NO: 10:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (xi) SEQUENCE DESCRIPTION: SEQ ID NO: 10:

```
ACTAGTCTGC TGATAGAAAG CACTATACAT CCTATTGTTT CTTTCTTTCC AAAATCAGCC      60
TTCTGTCTGT AACAAAAATG TACTTTATAG AGATGGAGGA AAAGGTCTAA TACTACATAG     120
CCTTAAGTGT TTCTGTCATT GTTCAAGTGT ATTTTCTGTA ACAGAAACAT ATTTGGAATG     180
TTTTTCTTTT CCCCTTATAA ATTGTAATTC CTGAAATACT GCTGCTTTAA AAAGTCCCAC     240
TGTCAGATTA TATTATCTAA CAATTGAATA TTGTAAATAT ACTTGTCTTA CCTCTCAATA     300
AAAGGGTACT TTTCTATTAN NNAGNNGNNN GNNNNATAAA ANAAAA                    346
```

(2) INFORMATION FOR SEQ ID NO: 11:

(i) SEQUENCE CHARACTERISTICS:
        (A) LENGTH: 602 base pairs
        (B) TYPE: nucleic acid
        (C) STRANDEDNESS: single
        (D) TOPOLOGY: linear (xi) SEQUENCE DESCRIPTION: SEQ ID NO: 11:

```
ACTAGTAAAA AGCAGCATTG CCAAATAATC CCTAATTTTC CACTAAAAAT ATAATGAAAT      60
GATGTTAAGC TTTTTGAAAA GTTAGGTTA AACCTACTGT TGTTAGATTA ATGTATTTGT     120
TGCTTCCCTT TATCTGGAAT GTGGCATTAG CTTTTTTATT TTAACCCTCT TTAATTCTTA     180
TTCAATTCCA TGACTTAAGG TTGGAGAGCT AAACACTGGG ATTTTTGGAT AACAGACTGA     240
CAGTTTTGCA TAATTATAAT CGGCATTGTA CATAGAAAGG ATATGGCTAC CTTTTGTTAA     300
ATCTGCACTT TCTAAATATC AAAAAAGGGA AATGAAGTTA TAAATCAATT TTTGTATAAT     360
CTGTTTGAAA CATGAGTTTT ATTTGCTTAA TATTAGGGCT TTGCCCCTTT TCTGTAAGTC     420
TCTTGGGATC CTGTGTAGAA CTGTTCTCAT TAAACACCAA ACAGTTAAGT CCATTCTCTG     480
```

```
GTACTAGCTA CAAATTCGGT TTCATATTCT ACTTAACAAT TTAAATAAAC TGAAATATTT      540

CTAGATGGTC TACTTCTGTT CATATAAAAA CAAAACTTGA TTTCCAAAAA AAAAAAAAAA      600

AA                                                                    602
```

(2) INFORMATION FOR SEQ ID NO: 12:

(i) SEQUENCE CHARACTERISTICS:
        (A) LENGTH: 685 base pairs
        (B) TYPE: nucleic acid
        (C) STRANDEDNESS: single
        (D) TOPOLOGY: linear (xi) SEQUENCE DESCRIPTION: SEQ ID NO: 12:

```
ACTAGTCCTG TGAAAGTACA ACTGAAGGCA GAAAGTGTTA GGATTTTGCA TCTAATGTTC       60

ATTATCATGG TATTGATGGA CCTAAGAAAA TAAAAATTAG ACTAAGCCCC CAAATAAGCT      120

GCATGCATTT GTAACATGAT TAGTAGATTT GAATATATAG ATGTAGTATN TTGGGTATCT      180

AGGTGTTTTA TCATTATGTA AAGGAATTAA AGTAAAGGAC TTTGTAGTTG TTTTTATTAA      240

ATATGCATAT AGTAGAGTGC AAAAATATAG CAAAAATANA AACTAAAGGT AGAAAAGCAT      300

TTTAGATATG CCTTAATNTA NNAACTGTGC CAGGTGGCCC TCGGAATAGA TGCCAGGCAG      360

AGACCAGTGC CTGGGTGGTG CCTCCCCTTG TCTGCCCCCC TGAAGAACTT CCCTCACGTG      420

ANGTAGTGCC CTCGTAGGTG TCACGTGGAN TANTGGGANC AGGCCGNNCN GTNANAAGAA      480

ANCANNGTGA NAGTTTCNCC GTNGANGCNG AACTGTCCCT GNGCCNNNAC GCTCCCANAA      540

CNTNTCCAAT NGACAATCGA GTTTCCNNNC TCCNGNAACC TNGCCGNNNN CNNGCCCNNC      600

CANTNTGNTA ACCCCGCGCC CGGATCGCTC TCNNNTCGTT CTCNCNCNAA NGGGNTTTCN      660

CNNCCGCCGT CNCNNCCCCG CNNCC                                           685
```

(2) INFORMATION FOR SEQ ID NO: 13:

(i) SEQUENCE CHARACTERISTICS:
        (A) LENGTH: 694 base pairs
        (B) TYPE: nucleic acid
        (C) STRANDEDNESS: single
        (D) TOPOLOGY: linear (xi) SEQUENCE DESCRIPTION: SEQ ID NO: 13:

```
CACTAGTCAC TCATTAGCGT TTTCAATAGG GCTCTTAAGT CCAGTAGATT ACGGGTAGTC       60

AGTTGACGAA GATCTGGTTT ACAAGAACTA ATTAAATGTT TCATTGCATT TTTGTAAGAA      120

CAGAATAATT TTATAAAATG TTTGTAGTTT ATAATTGCCG AAAATAATTT AAAGACACTT      180

TTTCTCTGTG TGTGCAAATG TGTGTTTGTG ATCCATTTTT TTTTTTTTTT TAGGACACCT      240

GTTTACTAGC TAGCTTTACA ATATGCCAAA AAAGGATTTC TCCCTGACCC CATCCGTGGT      300

TCACCCTCTT TTCCCCCCAT GCTTTTTGCC CTAGTTTATA ACAAAGGAAT GATGATGATT      360

TAAAAAGTAG TTCTGTATCT TCAGTATCTT GGTCTTCCAG AACCCTCTGG TTGGGAAGGG      420

GATCATTTTT TACTGGTCAT TTCCCTTTGG AGTGTACTAC TTTAACAGAT GGAAAGAACT      480

CATTGGCCAT GGAAACAGCC GANGTGTTGG GAGCCAGCAG TGCATGGCAC CGTCCGGCAT      540

CTGGCNTGAT TGGTCTGGCT GCCGTCATTG TCAGCACAGT GCCATGGGAC ATGGGGAANA      600

CTGACTGCAC NGCCAATGGT TTTCATGAAG AATACNGCAT NCNCNGTGAT CACGTNANCC      660

ANGACGCTAT GGGGGNCANA GGGCCANTTG CTTC                                 694
```

(2) INFORMATION FOR SEQ ID NO: 14:

(i) SEQUENCE CHARACTERISTICS:
    (A) LENGTH: 679 base pairs
    (B) TYPE: nucleic acid
    (C) STRANDEDNESS: single
    (D) TOPOLOGY: linear (xi) SEQUENCE DESCRIPTION: SEQ ID NO: 14:

| | | | | | | |
|---|---|---|---|---|---|---|
| CAGCCGCCTG | CATCTGTATC | CAGCGCCANG | TCCCGCCAGT | CCCAGCTGCG | CGCGCCCCCC | 60 |
| AGTCCCGNAC | CCGTTCGGCC | CANGCTNAGT | TAGNCCTCAC | CATNCCGGTC | AAAGGANGCA | 120 |
| CCAAGTGCAT | CAAATACCTG | CNGTNCGGAT | NTAAATTCAT | CTTCTGGCTT | GCCGGGATTG | 180 |
| CTGTCCNTGC | CATTGGACTA | NGGCTCCGAT | NCGACTCTCA | GACCANGANC | ATCTTCGANC | 240 |
| NAGANACTAA | TNATNATTNT | TCCAGCTTCT | ACACAGGAGT | CTATATTCTG | ATCGGATCCG | 300 |
| GCNCCCTCNT | GATGCTGGTG | GGCTTCCTGA | GCTGCTGCGG | GGCTGTGCAA | GAGTCCCANT | 360 |
| GCATGCTGGG | ACTGTTCTTC | GGCTTCNTCT | TGGTGATATN | CGCCATTGAA | ATACCTGCGG | 420 |
| CCATCTGGGG | ATATTCCACT | NCGATNATGT | GATTAAGGAA | NTCCACGGAG | TTTTACAAGG | 480 |
| ACACGTACAA | CNACCTGAAA | ACCNNGGATG | ANCCCCACCG | GGAANCNCTG | AANGCCATCC | 540 |
| ACTATGCGTT | GAACTGCAAT | GGTTTGGCTG | GGGNCCTTGA | ACAATTTAAT | CNCATACATC | 600 |
| TGGCCCCANN | AAAGGACNTN | CTCGANNCCT | TCNCCGTGNA | ATTCNGTTCT | GATNCCATCA | 660 |
| CAGAAGTCTC | GAACAATCC | | | | | 679 |

(2) INFORMATION FOR SEQ ID NO: 15:

(i) SEQUENCE CHARACTERISTICS:
    (A) LENGTH: 695 base pairs
    (B) TYPE: nucleic acid
    (C) STRANDEDNESS: single
    (D) TOPOLOGY: linear (xi) SEQUENCE DESCRIPTION: SEQ ID NO: 15:

| | | | | | | |
|---|---|---|---|---|---|---|
| ACTAGTGGAT | AAAGGCCAGG | GATGCTGCTC | AACCTCCTAC | CATGTACAGG | GACGTCTCCC | 60 |
| CATTACAACT | ACCCAATCCG | AAGTGTCAAC | TGTGTCAGGA | CTAANAAACC | CTGGTTTTGA | 120 |
| TTAAAAAAGG | GCCTGAAAAA | AGGGGAGCCA | CAAATCTGTC | TGCTTCCTCA | CNTTANTCNT | 180 |
| TGGCAAATNA | GCATTCTGTC | TCNTTGGCTG | CNGCCTCANC | NCAAAAAANC | NGAACTCNAT | 240 |
| CNGGCCCAGG | AATACATCTC | NCAATNAACN | AAATTGANCA | AGGCNNTGGG | AAATGCCNGA | 300 |
| TGGGATTATC | NTCCGCTTGT | TGANCTTCTA | AGTTTCNTTC | CCTTCATTCN | ACCCTGCCAG | 360 |
| CCNAGTTCTG | TTAGAAAAAT | GCCNGAATTC | NAACNCCGGT | TTTCNTACTC | NGAATTTAGA | 420 |
| TCTNCANAAA | CTTCCTGGCC | ACNATTCNAA | TTNANGGNCA | CGNACANATN | CCTTCCATNA | 480 |
| ANCNCACCCC | ACNTTTGANA | GCCANGACAA | TGACTGCNTN | AANTGAAGGC | NTGAAGGAAN | 540 |
| AACTTTGAAA | GGAAAAAAAA | CTTTGTTTCC | GGCCCCTTCC | AACNCTTCTG | TGTTNANCAC | 600 |
| TGCCTTCTNG | NAACCCTGGA | AGCCCNGNGA | CAGTGTTACA | TGTTGTTCTA | NNAAACNGAC | 660 |
| NCTTNAATNT | CNATCTTCCC | NANAACGATT | NCNCC | | | 695 |

(2) INFORMATION FOR SEQ ID NO: 16:

(i) SEQUENCE CHARACTERISTICS:
    (A) LENGTH: 669 base pairs
    (B) TYPE: nucleic acid
    (C) STRANDEDNESS: single
    (D) TOPOLOGY: linear (xi) SEQUENCE DESCRIPTION: SEQ ID NO: 16:

| | | | | | | |
|---|---|---|---|---|---|---|
| CGCCGAAGCA | GCAGCGCAGG | TTGTCCCCGT | TTCCCCTCCC | CCTTCCCTTC | TCCGGTTGCC | 60 |

```
TTCCCGGGCC CCTTACACTC CACAGTCCCG GTCCCGCCAT GTCCCAGAAA CAAGAAGAAG      120

AGAACCCTGC GGAGGAGACC GGCGAGGAGA AGCAGGACAC GCAGGAGAAA GAAGGTATTC      180

TGCCTGAGAG AGCTGAAGAG GCAAAGCTAA AGGCCAAATA CCCAAGCCTA GGACAAAAGC      240

CTGGAGGCTC CGACTTCCTC ATGAAGAGAC TCCAGAAAGG GCAAAAGTAC TTTGACTCNG      300

GAGACTACAA CATGGCCAAA GCCAACATGA AGAATAAGCA GCTGCCAAGT GCANGACCAG      360

ACAAGAACCT GGTGACTGGT GATCACATCC CCACCCCACA GGATCTGCCC AGAGAAAGTC      420

CTCGCTCGTC ACCAGCAAGC TTGCGGGTGG CCAAGTTGAA TGATGCTGCC GGGGCTCTGC      480

CANATCTGAG ACGCTTCCCT CCCTGCCCCA CCCGGGTCCT GTGCTGGCTC CTGCCCTTCC      540

TGCTTTTGCA GCCANGGGTC AGGAAGTGGC NCNGGTNGTG GCTGGAAAGC AAAACCCTTT      600

CCTGTTGGTG TCCCACCCAT GGAGCCCCTG GGGCGAGCCC ANGAACTTGA NCCTTTTTGT      660

TNTCTTNCC                                                             669

(2) INFORMATION FOR SEQ ID NO: 17:

(i) SEQUENCE CHARACTERISTICS:
        (A) LENGTH: 697 base pairs
        (B) TYPE: nucleic acid
        (C) STRANDEDNESS: single
        (D) TOPOLOGY: linear (xi) SEQUENCE DESCRIPTION: SEQ ID NO: 17:

GCAAGATATG GACAACTAAG TGAGAAGGTA ATNCTCTACT GCTCTAGNTN CTCCNGGCNN       60

GACGCGCTGA GGAGANNNAC GCTGGCCCAN CTGCCGGCCA CACACGGGGA TCNTGGTNAT      120

GCCTGCCCAN GGGANCCCCA NCNCTCGGAN CCCATNTCAC ACCCGNNCCN TNCGCCCACN      180

NCCTGGCTCN CNCNGCCCNG NCCAGCTCNC GNCCCCCTCC GCCNNNCTCN TTNNCNTCTC      240

CNCNCCCTCC NCNACNACCT CCTACCCNCG GCTCCCTCCC CAGCCCCCCC CCGCAANCCT      300

CCACNACNCC NTCNNCNCGA ANCNCCNCTC GCNCTCNGCC CCNGCCCCCT GCCCCCCGCC      360

CNCNACNNCG CGNTCCCCCG CGCNCGCNGC CTCNCCCCCT CCCACNACAG NCNCACCCGC      420

AGNCACGCNC TCCGCCCNCT GACGCCCCNN CCCGCCGCGC TCACCTTCAT GGNCCNACNG      480

CCCCGCTCNC NCCNCTGCNC GCCGNCNNGG CGCCCCGCCC CNNCCGNGTN CCNCNCGNNG      540

CCCCNGCNGN ANGCNGTGCG CNNCANGNCC GNGCCGNNCN NCACCCTCCG NCCNCCGCCC      600

CGCCCGCTGG GGGCTCCCGC CNCGCGGNTC ANTCCCCNCC CNTNCGCCCA CTNTCCGNTC      660

CNNCNCTCNC GCTCNGCGCN CGCCCNCCNC CCCCCCC                              697

(2) INFORMATION FOR SEQ ID NO: 18:

(i) SEQUENCE CHARACTERISTICS:
        (A) LENGTH: 670 base pairs
        (B) TYPE: nucleic acid
        (C) STRANDEDNESS: single
        (D) TOPOLOGY: linear (xi) SEQUENCE DESCRIPTION: SEQ ID NO: 18:

CTCGTGTGAA GGGTGCAGTA CCTAAGCCGG AGCGGGGTAG AGGCGGGCCG GCACCCCCTT       60

CTGACCTCCA GTGCCGCCGG CCTCAAGATC AGACATGGCC CAGAACTTGA ACGACTTGGC      120

GGGACGGCTG CCCGCCGGGC CCCGGGGCAT GGGCACGGCC CTGAAGCTGT TGCTGGGGGC      180

CGGCGCCGTG GCCTACGGTG TGCGCGAATC TGTGTTCACC GTGGAAGGCG GGCNCAGAGC      240

CATCTTCTTC AATCGGATCG GTGGAGTGCA CAGGACACTA TCCTGGGCCG ANGGCCTTCA      300
```

```
CTTCAGGATC CTTGGTTCCA GTACCCCANC ATCTATGACA TTCGGGCCAG ACCTCGAAAA      360

AATCTCCTCC CTACAGGCTC CAAAGACCTA CAGATGGTGA ATATCTCCCT GCGAGTGTTG      420

TCTCGACCAA TGCTCANGAA CTTCCTAACA TGTTCCANCG CCTAAGGGCT GGACTACNAA      480

GAACGANTGT TGCCGTCCAT TGTCACGAAG TGCTCAAGAA TTTNGGTGGC CAAGTTCAAT      540

GNCCTCACNN CTGATCNCCC AGCGGGGCCA AGTTANCCCT GGTTGATCCC CGGGGANCTG      600

ACNNAAAAGG GCCAAGGACT TCCCCTCATC CTGGATAATG TGGCCNTCAC AAAGCTCAAC      660

TTTANCCACC                                                            670
```

(2) INFORMATION FOR SEQ ID NO: 19:

(i) SEQUENCE CHARACTERISTICS:
        (A) LENGTH: 606 base pairs
        (B) TYPE: nucleic acid
        (C) STRANDEDNESS: single
        (D) TOPOLOGY: linear (xi) SEQUENCE DESCRIPTION: SEQ ID NO: 19:

```
ACTAGTGCCA ACCTCAGCTC CCAGGCCAGT TCTCTGAATG TCGAGGAGTT CCAGGATCTC       60

TGGCCTCAGT TGTCCTTGGT TATTGATGGG GGACAAATTG GGGATGGCCA GAGCCCCGAG      120

TGTCGCCTTG GCTCAACTGT GGTTGATTTG TCTGTGCCCG GAAAGTTTGG CATCATTCGT      180

CCAGGCTGTG CCCTGGAAAG TACTACAGCC ATCCTCCAAC AGAAGTACGG ACTGCTCCCC      240

TCACATGCGT CCTACCTGTG AAACTCTGGG AAGCAGGAAG GCCCAAGACC TGGTGCTGGA      300

TACTATGTGT CTGTCCACTG ACGACTGTCA AGGCCTCATT TGCAGAGGCC ACCGGAGCTA      360

GGGCACTAGC CTGACTTTTA AGGCAGTGTG TCTTTCTGAG CACTGTAGAC CAAGCCCTTG      420

GAGCTGCTGG TTTAGCCTTG CACCTGGGGA AAGGATGTAT TTATTTGTAT TTTCATATAT      480

CAGCCAAAAG CTGAATGGAA AAGTTNAGAA CATTCCTAGG TGGCCTTATT CTAATAAGTT      540

TCTTCTGTCT GTTTTGTTTT TCAATTGAAA AGTTATTAAA TAACAGATTT AGAATCTAGT      600

GAGACC                                                                606
```

(2) INFORMATION FOR SEQ ID NO: 20:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (xi) SEQUENCE DESCRIPTION: SEQ ID NO:20:

```
ACTAGTAAAC AACAGCAGCA GAAACATCAG TATCAGCAGC GTCGCCAGCA GGAGAATATG       60

CAGCGCCAGA GCCGAGGAGA ACCCCCGCTC CCTGAGGAGG ACCTGTCCAA ACTCTTCAAA      120

CCACCACAGC CGCCTGCCAG GATGGACTCG CTGCTCATTG CAGGCCAGAT AAACACTTAC      180

TGCCAGAACA TCAAGGAGTT CACTGCCCAA AACTTAGGCA AGCTCTTCAT GGCCCAGGCT      240

CTTCAAGAAT ACAACAACTA AGAAAAGGAA GTTCCAGAA AAGAAGTTAA CATGAACTCT       300

TGAAGTCACA CCAGGGCAAC TCTTGGAAGA AATATATTTG CATATTGAAA AGCACAGAGG      360

ATTTCTTTAG TGTCATTGCC GATTTTGGCT ATAACAGTGT CTTTCTAGCC ATAATAAAAT      420

AAAACAAAAT CTTGACTGCT TGCTCAAAA                                        449
```

(2) INFORMATION FOR SEQ ID NO: 21:

(i) SEQUENCE CHARACTERISTICS:
        (A) LENGTH: 409 base pairs (B) TYPE: nucleic acid
        (C) STRANDEDNESS: single
        (D) TOPOLOGY: linear (xi) SEQUENCE DESCRIPTION: SEQ ID NO: 21:

| | | |
|---|---|---|
| TATCAATCAA CTGGTGAATA ATTAAACAAT GTGTGGTGTG ATCATACAAA GGGTACCACT | 60 |
| CAATGATAAA AGGAACAAGC TGCCTATATG TGGAACAACA TGGATGCATT TCAGAAACTT | 120 |
| TATGTTGAGT GAAAGAACAA ACACGGAGAA CATACTATGT GGTTCTCTTT ATGTAACATT | 180 |
| ACAGAAATAA AAACAGAGGC AACCACCTTT GAGGCAGTAT GGAGTGAGAT AGACTGGAAA | 240 |
| AAGGAAGGAA GGAAACTCTA CGCTGATGGA AATGTCTGTG TCTTCATTGG GTGGTAGTTA | 300 |
| TGTGGGATA TACATTTGTC AAAATTTATT GAACTATATA CTAAAGAACT CTGCATTTTA | 360 |
| TTGGGATGTA ATAATACCT CAATTAAAAA GACAAAAAAA AAAAAAAA | 409 |

(2) INFORMATION FOR SEQ ID NO: 22:

(i) SEQUENCE CHARACTERISTICS:
        (A) LENGTH: 649 base pairs
        (B) TYPE: nucleic acid
        (C) STRANDEDNESS: single
        (D) TOPOLOGY: linear (xi) SEQUENCE DESCRIPTION: SEQ ID NO: 22:

| | | |
|---|---|---|
| ACAATTTTCA TTATCTTAAG CACATTGTAC ATTTCTACAG AACCTGTGAT TATTCTCGCA | 60 |
| TGATAAGGAT GGTACTTGCA TATGGTGAAT TACTACTGTT GACAGTTTCC GCAGAAATCC | 120 |
| TATTTCAGTG GACCAACATT GTGGCATGGC AGCAAATGCC AACATTTTGT GGAATAGCAG | 180 |
| CAAATCTACA AGAGACCCTG GTTGGTTTTT CGTTTTGTTT TCTTTGTTTT TTCCCCCTTC | 240 |
| TCCTGAATCA GCAGGGATGG AANGAGGGTA GGGAAGTTAT GAATTACTCC TTCCAGTAGT | 300 |
| AGCTCTGAAG TGTCACATTT AATATCAGTT TTTTTAAAC ATGATTCTAG TTNAATGTAG | 360 |
| AAGAGAGAAG AAAGAGGAAG TGTTCACTTT TTTAATACAC TGATTTAGAA ATTTGATGTC | 420 |
| TTATATCAGT AGTTCTGAGG TATTGATAGC TTGCTTTATT TCTGCCTTTA CGTTGACAGT | 480 |
| GTTGAAGCAG GGTGAATAAC TAGGGCATA TATATTTTTT TTTTTTGTAA GCTGTTTCAT | 540 |
| GATGTTTTCT TTGGAATTTC CGGATAAGTT CAGGAAAACA TCTGCATGTT GTTATCTAGT | 600 |
| CTGAAGTTCN TATCCATCTC ATTACAACAA AAACNCCCAG AACGGNTTG | 649 |

(2) INFORMATION FOR SEQ ID NO: 23:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (xi) SEQUENCE DESCRIPTION: SEQ ID NO: 23:

| | | |
|---|---|---|
| ACTAGTGCCG TACTGGCTGA ATCCCTGCA GGACCAGGAA GAGAACCAGT TCAGACTTTG | 60 |
| TACTCTCAGT CACCAGCTCT GGAATTAGAT AAATTCCTTG AAGATGTCAG GAATGGGATC | 120 |
| TATCCTCTGA CAGCCTTTGG GCTGCCTCGG CCCCAGCAGC CACAGCAGGA GGAGGTGACA | 180 |
| TCACCTGTCG TGCCCCCCTC TGTCAAGACT CCGACACCTG AACCAGCTGA GGTGGAGACT | 240 |
| CGCAAGGTGG TGCTGATGCA GTGCAACATT GAGTCGGTGG AGGAGGGAGT CAAACACCAC | 300 |
| CTGACACTTC TGCTGAAGTT GGAGGACAAA CTGAACCGGC ACCTGAGCTG TGACCTGATG | 360 |
| CCAAATGAGA ATATCCCCGA GTTGGCGGCT GAGCTGGTGC AGCTGGGCTT CATTAGTGAG | 420 |
| GCTGACCAGA GCCGGTTGAC TTCTCTGCTA GAAGAGACTT GAACAAGTTC AATTTTGCCA | 480 |

```
GGAACAGTAC CCTCAACTCA GCCGCTGTCA CCGTCTCCTC TTAGAGCTCA CTCGGGCCAG      540

GCCCTGATCT GCGCTGTGGC TGTCCTGGAC GTGCTGCACC CTCTGTCCTT CCCCCCAGTC      600

AGTATTACCT GTGAAGCCCT TCCCTCCTTT ATTATTCAGG ANGGCTGGGG GGGCTCCTTG      660

NTTCTAACC                                                              669
```

(2) INFORMATION FOR SEQ ID NO: 24:

(i) SEQUENCE CHARACTERISTICS:
        (A) LENGTH: 442 base pairs
        (B) TYPE: nucleic acid
        (C) STRANDEDNESS: single
        (D) TOPOLOGY: linear (xi) SEQUENCE DESCRIPTION: SEQ ID NO: 24:

```
ACTAGTACCA TCTTGACAGA GGATACATGC TCCCAAAACG TTTGTTACCA CACTTAAAAA       60

TCACTGCCAT CATTAAGCAT CAGTTTCAAA ATTATAGCCA TTCATGATTT ACTTTTTCCA      120

GATGACTATC ATTATTCTAG TCCTTTGAAT TTGTAAGGGG AAAAAAAACA AAAACAAAAA      180

CTTACGATGC ACTTTTCTCC AGCACATCAG ATTTCAAATT GAAAATTAAA GACATGCTAT      240

GGTAATGCAC TTGCTAGTAC TACACACTTT GGTACAACAA AAAACAGAGG CAAGAAACAA      300

CGGAAAGAGA AAAGCCTTCC TTTGTTGGCC CTTAAACTGA GTCAAGATCT GAAATGTAGA      360

GATGATCTCT GACGATACCT GTATGTTCTT ATTGTGTAAA TAAAATTGCT GGTATGAAAT      420

GACCTAAAAA AAAAAAAGA AA                                                442
```

(2) INFORMATION FOR SEQ ID NO: 25:

(i) SEQUENCE CHARACTERISTICS:
        (A) LENGTH: 656 base pairs
        (B) TYPE: nucleic acid
        (C) STRANDEDNESS: single
        (D) TOPOLOGY: linear (xi) SEQUENCE DESCRIPTION: SEQ ID NO: 25:

```
TGCAAGTACC ACACACTGTT TGAATTTTGC ACAAAAAGTG ACTGTAGGAT CAGGTGATAG       60

CCCCGGAATG TACAGTGTCT TGGTGCACCA AGATGCCTTC TAAAGGCTGA CATACCTTGG      120

ACCCTAATGG GGCAGAGAGT ATAGCCCTAG CCCAGTGGTG ACATGACCAC TCCCTTTGGG      180

AGGCCTGAGG TAGAGGGGAG TGGTATGTGT TTTCTCAGTG GAAGCAGCAC ATGAGTGGGT      240

GACAGGATGT TAGATAAAGG CTCTAGTTAG GGTGTCATTG TCATTTGAGA GACTGACACA      300

CTCCTAGCAG CTGGTAAAGG GGTGCTGGAN GCCATGGAGG ANCTCTAGAA ACATTAGCAT      360

GGGCTGATCT GATTACTTCC TGGCATCCCG CTCACTTTTA TGGGAAGTCT TATTAGANGG      420

ATGGGACAGT TTTCCATATC CTTGCTGTGG AGCTCTGGAA CACTCTCTAA ATTTCCCTCT      480

ATTAAAAATC ACTGCCCTAA CTACACTTCC TCCTTGAAGG AATAGAAATG GAACTTTCTC      540

TGACATANTT CTTGGCATGG GGAGCCAGCC ACAAATGANA ATCTGAACGT GTCCAGGTTT      600

CTCCTGANAC TCATCTACAT AGAATTGGTT AAACCCTCCC TTGGAATAAG GAAAAA         656
```

(2) INFORMATION FOR SEQ ID NO: 26:

(i) SEQUENCE CHARACTERISTICS:
        (A) LENGTH: 434 base pairs
        (B) TYPE: nucleic acid
        (C) STRANDEDNESS: single
        (D) TOPOLOGY: linear (xi) SEQUENCE DESCRIPTION: SEQ ID NO: 26:

ACTAGTTCAG ACTGCCACGC CAACCCCAGA AAATACCCCA CATGCCAGAA AAGTGAAGTC    60

CTAGGTGTTT CCATCTATGT TTCAATCTGT CCATCTACCA GGCCTCGCGA TAAAAACAAA   120

ACAAAAAAAC GCTGCCAGGT TTTAGAAGCA GTTCTGGTCT CAAAACCATC AGGATCCTGC   180

CACCAGGGTT CTTTTGAAAT AGTACCACAT GTAAAAGGGA ATTTGGCTTT CACTTCATCT   240

AATAACTGAA TTGTCAGGCT TTGATTGATA ATTGTAGAAA TAAGTAGCCT TCTGTTGTGG   300

GAATAAGTTA TAATCAGTAT TCATCTCTTT GTTTTTTGTC ACTCTTTTCT CTCTAATTGT   360

GTCATTTGTA CTGTTTGAAA AATATTTCTT CTATNAAATT AAACTAACCT GCCTTAAAAA   420

AAAAAAAAAA AAAA   434

(2) INFORMATION FOR SEQ ID NO: 27:

(i) SEQUENCE CHARACTERISTICS:
        (A) LENGTH: 654 base pairs
        (B) TYPE: nucleic acid
        (C) STRANDEDNESS: single
        (D) TOPOLOGY: linear (xi) SEQUENCE DESCRIPTION: SEQ ID NO: 27:

ACTAGTCCAA CACAGTCAGA AACATTGTTT TGAATCCTCT GTAAACCAAG GCATTAATCT    60

TAATAAACCA GGATCCATTT AGGTACCACT TGATATAAAA AGGATATCCA TAATGAATAT   120

TTTATACTGC ATCCTTTACA TTAGCCACTA AATACGTTAT TGCTTGATGA AGACCTTTCA   180

CAGAATCCTA TGGATTGCAG CATTTCACTT GGCTACTTCA TACCCATGCC TTAAAGAGGG   240

GCAGTTTCTC AAAAGCAGAA ACATGCCGCC AGTTCTCAAG TTTTCCTCCT AACTCCATTT   300

GAATGTAAGG GCAGCTGGCC CCCAATGTGG GGAGGTCCGA ACATTTTCTG AATTCCCATT   360

TTCTTGTTCG CGGCTAAATG ACAGTTTCTG TCATTACTTA GATTCCGATC TTTCCCAAAG   420

GTGTTGATTT ACAAGAGGC CAGCTAATAG CAGAAATCAT GACCCTGAAA GAGAGATGAA   480

ATTCAAGCTG TGAGCCAGGC AGGANCTCAG TATGGCAAAG GTCTTGAGAA TCNGCCATTT   540

GGTACAAAAA AAATTTTAAA GCNTTTATGT TATACCATGG AACCATAGAA ANGGCAAGGG   600

AATTGTTAAG AANAATTTTA AGTGTCCAGA CCCANAANGA AAAAAAAAA AAAA   654

(2) INFORMATION FOR SEQ ID NO: 28:

(i) SEQUENCE CHARACTERISTICS:
        (A) LENGTH: 670 base pairs
        (B) TYPE: nucleic acid
        (C) STRANDEDNESS: single
        (D) TOPOLOGY: linear (xi) SEQUENCE DESCRIPTION: SEQ ID NO: 28:

CGTGTGCACA TACTGGGAGG ATTTCCACAG CTGCACGGTC ACAGCCCTTA CGGATTGCCA    60

GGAAGGGGCG AAAGATATGT GGGATAAACT GAGAAAAGAA NCCAAAAACC TCAACATCCA   120

AGGCAGCTTA TTCGAACTCT GCGGCAGCGG CAACGGGGCG GCGGGGTCCC TGCTCCCGGC   180

GTTCCCGGTG CTCCTGGTGT CTCTCTCGGC AGCTTTAGCG ACCTGNCTTT CCTTCTGAGC   240

GTGGGGCCAG CTCCCCCCGC GGCGCCCACC CACNCTCACT CCATGCTCCC GGAAATCGAG   300

AGGAAGATCA TTAGTTCTTT GGGGACGTTN GTGATTCTCT GTGATGCTGA AAACACTCA   360

TATAGGGAAT GTGGGAAATC CTGANCTCTT TNTTATNTCG TNTGATTTCT TGTGTTTTAT   420

TTGCCAAAAT GTTACCAATC AGTGACCAAC CNAGCACAGC CAAAAATCGG ACNTCNGCTT   480

TAGTCCGTCT TCACACACAG AATAAGAAAA CGGCAAACCC ACCCCACTTT TNANTTTNAT   540

```
TATTACTAAN TTTTTTCTGT TGGGCAAAAG AATCTCAGGA ACNGCCCTGG GGCCNCCGTA      600

CTANAGTTAA CCNAGCTAGT TNCATGAAAA ATGATGGGCT CCNCCTCAAT GGGAAAGCCA      660

AGAAAAAGNC                                                             670

(2) INFORMATION FOR SEQ ID NO: 29:

(i) SEQUENCE CHARACTERISTICS:
        (A) LENGTH: 551 base pairs
        (B) TYPE: nucleic acid
        (C) STRANDEDNESS: single
        (D) TOPOLOGY: linear (xi) SEQUENCE DESCRIPTION: SEQ ID NO: 29:

ACTAGTCCTC CACAGCCTGT GAATCCCCCT AGACCTTTCA AGCATAGTGA GCGGAGAAGA       60

AGATCTCAGC GTTTAGCCAC CTTACCCATG CCTGATGATT CTGTAGAAAA GGTTTCTTCT      120

CCCTCTCCAG CCACTGATGG GAAAGTATTC TCCATCAGTT CTCAAAATCA GCAAGAATCT      180

TCAGTACCAG AGGTGCCTGA TGTTGCACAT TTGCCACTTG AGAAGCTGGG ACCCTGTCTC      240

CCTCTTGACT TAAGTCGTGG TTCAGAAGTT ACAGCACCGG TAGCCTCAGA TTCCTCTTAC      300

CGTAATGAAT GTCCCAGGGC AGAAAAAGAG GATACNCAGA TGCTTCCAAA TCCTTCTTCC      360

AAAGCAATAG CTGATGGGAA GAGGAGCTCC AGCAGCAGCA GGAATATCGA AAACAGAAAA      420

AAAAGTGAAA TTGGGAAGAC AAAAGCTCAA CAGCATTTGG TAAGGAGAAA AGANAAGATG      480

AGGAAGGAAG AGAGAAGAGA GACNAAGATC NCTACGGACC GNNNCGGAAG AAGAAGAAGN      540

AAAAAANAAA A                                                          551

(2) INFORMATION FOR SEQ ID NO: 30:

(i) SEQUENCE CHARACTERISTICS:
        (A) LENGTH: 684 base pairs
        (B) TYPE: nucleic acid
        (C) STRANDEDNESS: single
        (D) TOPOLOGY: linear (xi) SEQUENCE DESCRIPTION: SEQ ID NO: 30:

ACTAGTTCTA TCTGGAAAAA GCCCGGGTTG GAAGAAGCTG TGGAGAGTGC GTGTGCAATG       60

CGAGACTCAT TTCTTGGAAG CATCCCTGGC AAAAATGCAG CTGAGTACAA GGTTATCACT      120

GTGATAGAAC CTGGACTGCT TTTTGAGATA ATAGAGATGC TGCAGTCTGA AGAGACTTCC      180

AGCACCTCTC AGTTGAATGA ATTAATGATG GCTTCTGAGT CAACTTTACT GGCTCAGGAA      240

CCACGAGAGA TGACTGCAGA TGTAATCGAG CTTAAAGGGA AATTCCTCAT CAACTTAGAA      300

GGTGGTGATA TTCGTGAAGA GTCTTCCTAT AAAGTAATTG TCATGCCGAC TACGAAAGAA      360

AAATGCCCCC GTTGTTGGAA GTATACAGCG GGAGTCTTCA GATACACTGT GTCCTCGATG      420

TGCAGAAGTT GTCAGTGGGA AAATAGTATT AACAGCTCAC TCGAGCAAGA ACCCTCCTGA      480

CAGTACTGGG CTAGAAGTTT GGATGGATTA TTTACAATAT AGGAAAGAAA GCCAAGAATT      540

AGGTNATGAG TGGATGAGTA AATGGTGGAN GATGGGGAAT TCAAATCAGA ATTATGGAAG      600

AAGTTNTTCC TGTTACTATA GAAAGGAATT ATGTTTATTT ACATGCAGAA AATATANATG      660

TGTGGTGTGT ACCGTGGATG GAAN                                            684

(2) INFORMATION FOR SEQ ID NO: 31:

(i) SEQUENCE CHARACTERISTICS:
        (A) LENGTH: 654 base pairs
        (B) TYPE: nucleic acid
        (C) STRANDEDNESS: single
```

(D) TOPOLOGY: linear (xi) SEQUENCE DESCRIPTION: SEQ ID NO: 31:

| | | | | | |
|---|---|---|---|---|---|
| GCGCAGAAAA | GGAACCAATA | TTTCAGAAAC | AAGCTTAATA | GGAACAGCTG | CCTGTACATC | 60 |
| AACATCTTCT | CAGAATGACC | CAGAAGTTAT | CATCGTGGGA | GCTGGCGTGC | TTGGCTCTGC | 120 |
| TTTGGCAGCT | GTGCTTTCCA | GAGATGGAAG | AAAGGTGACA | GTCATTGAGA | GAGACTTAAA | 180 |
| AGAGCCTGAC | AGAATAGTTG | GAGAATTCCT | GCAGCCGGGT | GGTTATCATG | TTCTCAAAGA | 240 |
| CCTTGGTCTT | GGAGATACAG | TGGAAGGTCT | TGATGCCCAG | GTTGTAAATG | GTTACATGAT | 300 |
| TCATGATCAG | GGAAAGCAAA | TCAGANGTTC | AGATTCCTTA | CCCTCTGTCA | GAAAACAATC | 360 |
| AAGTGCAGAG | TGGAAGAGCT | TTCCATCACG | GAAGATTCAT | CATGAGTCTC | CGGAAAGCAG | 420 |
| CTATGGCAGA | GCCCAATGCA | AAGTTTATTG | AAGGTGTTGT | GTTACAGTTA | TTAGAGGAAG | 480 |
| ATGATGTTGT | GATGGGAGTT | CAGTACAAGG | ATAAAGAGAC | TGGGAGATAT | CAAGGAACTC | 540 |
| CATGCTCCAC | TGACTGTTGT | TGCAGATGGG | CTTTTCTCCA | ANTTCAGGAA | AAGCCTGGTC | 600 |
| TCAATAAAGT | TTCTGTATCA | CTCATTTGGT | TGGCTTCTTA | TGAAGAATGC | NCCC | 654 |

(2) INFORMATION FOR SEQ ID NO: 32:

(i) SEQUENCE CHARACTERISTICS:
        (A) LENGTH: 673 base pairs
        (B) TYPE: nucleic acid
        (C) STRANDEDNESS: single
        (D) TOPOLOGY: linear (xi) SEQUENCE DESCRIPTION: SEQ ID NO: 32:

| | | | | | |
|---|---|---|---|---|---|
| ACTAGTGAAG | AAAAGAAAT | TCTGATACGG | GACAAAAATG | CTCTTCAAAA | CATCATTCTT | 60 |
| TATCACCTGA | CACCAGGAGT | TTTCATTGGA | AAAGGATTTG | AACCTGGTGT | TACTAACATT | 120 |
| TTAAAGACCA | CACAAGGAAG | CAAAATCTTT | CTGAAAGAAG | TAAATGATAC | ACTTCTGGTG | 180 |
| AATGAATTGA | AATCAAAAGA | ATCTGACATC | ATGACAACAA | ATGGTGTAAT | TCATGTTGTA | 240 |
| GATAAACTCC | TCTATCCAGC | AGACACACCT | GTTGGAAATG | ATCAACTGCT | GGAAATACTT | 300 |
| AATAAATTAA | TCAAATACAT | CCAAATTAAG | TTTGTTCGTG | GTAGCACCTT | CAAAGAAATC | 360 |
| CCCGTGACTG | TCTATNAGCC | AATTATTAAA | AAATACACCA | AAATCATTGA | TGGGAGTGCC | 420 |
| TGTGGGAAAT | AACTGAAAAA | GAGACCGAGA | AGAACGAATC | ATTACAGGTC | CTGAAATAAA | 480 |
| ATACCTAGGA | TTTCTACTGG | AGGTGGAGAA | ACAGAAGAAC | TCTGAAGAAA | TTGTTACAAG | 540 |
| AAGANGTCCC | AAGGTCACCA | AATTCATTGA | AGGTGGTGAT | GGTCTTTATT | TGAAGATGAA | 600 |
| GAAATTAAAA | GACGCTTCAG | GGAGACNCCC | CATGAAGGAA | TTGCCAGCCA | CAAAAAAATT | 660 |
| CAGGGATTAG | AAA | | | | | 673 |

(2) INFORMATION FOR SEQ ID NO: 33:

(i) SEQUENCE CHARACTERISTICS:
        (A) LENGTH: 673 base pairs
        (B) TYPE: nucleic acid
        (C) STRANDEDNESS: single
        (D) TOPOLOGY: linear (xi) SEQUENCE DESCRIPTION: SEQ ID NO: 33:

| | | | | | |
|---|---|---|---|---|---|
| ACTAGTTATT | TACTTTCCTC | CGCTTCAGAA | GGTTTTTCAG | ACTGAGAGCC | TAAGCATACT | 60 |
| GGATCTGTTG | TTTCTTTTGG | GTCTCACCTC | ATCAGTGTGC | ATAGTGGCAG | AAATTATAAA | 120 |
| GAAGGTTGAA | AGGAGCAGGG | AAAAGATCCA | GAAGCATGTT | AGTTCGACAT | CATCATCTTT | 180 |
| TCTTGAAGTA | TGATGCATAT | TGCATTATTT | TATTTGCAAA | CTAGGAATTG | CAGTCTGAGG | 240 |

```
ATCATTTAGA AGGGCAAGTT CAAGAGGATA TGAAGATTTG AGAACTTTTT AACTATTCAT      300

TGACTAAAAA TGAACATTAA TGTTNAAGAC TTAAGACTTT AACCTGCTGG CAGTCCCAAA      360

TGAAATTATG CAACTTTGAT ATCATATTCC TTGATTTAAA TTGGGCTTTT GTGATTGANT      420

GAAACTTTAT AAAGCATATG GTCAGTTATT TNATTAAAAA GGCAAAACCT GAACCACCTT      480

CTGCACTTAA AGAAGTCTAA CAGTACAAAT ACCTATCTAT CTTAGATGGA TNTATTTNTT      540

TNTATTTTTA AATATTGTAC TATTTATGGT NGGTGGGGCT TTCTTACTAA TACACAAATN      600

AATTTATCAT TTCAANGGCA TTCTATTTGG GTTTAGAAGT TGATTCCAAG NANTGCATAT      660

TTCGCTACTG TNT                                                         673
```

(2) INFORMATION FOR SEQ ID NO: 34:

(i) SEQUENCE CHARACTERISTICS:
        (A) LENGTH: 684 base pairs
        (B) TYPE: nucleic acid
        (C) STRANDEDNESS: single
        (D) TOPOLOGY: linear (xi) SEQUENCE DESCRIPTION: SEQ ID NO: 34:

```
ACTAGTTTAT TCAAGAAAAG AACTTACTGA TTCCTCTGTT CCTAAAGCAA GAGTGGCAGG       60

TGATCAGGGC TGGTGTAGCA TCCGGTTCCT TTAGTGCAGC TAACTGCATT TGTCACTGAT      120

GACCAAGGAG GAAATCACTA AGACATTTGA GAAGCAGTGG TATGAACGTT CTTGGACAAG      180

CCACAGTTCT GAGCCTTAAC CCTGTAGTTT GCACACAAGA ACGAGCTCCA CCTCCCCTTC      240

TTCAGGAGGA ATCTGTGCGG ATAGATTGGC TGGACTTTTC AATGGTTCTG GGTTGCAAGT      300

GGGCACTGTT ATGGCTGGGT ATGGAGCGGA CAGCCCCAGG AATCAGAGCC TCAGCCCGGC      360

TGCCTGGTTG GAAGGTACAG GTGTTCAGCA CCTTCGGAAA AAGGGCATAA AGTNGTGGGG      420

GACAATTCTC AGTCCAAGAA GAATGCATTG ACCATTGCTG GCTATTTGCT TNCCTAGTAN      480

GAATTGGATN CATTTTTGAC CANGATNNTT CTNCTATGCT TTNTTGCAAT GAAATCAAAT      540

CCCGCATTAT CTACAAGTGG TATGAAGTCC TGCNNCCCCC AGAGAGGCTG TTCAGGCNAT      600

GTCTTCCAAG GGCAGGGTGG GTTACACCAT TTTACCTCCC CTCTCCCCCC AGATTATGNA      660

CNCAGAAGGA ATTTNTTTCC TCCC                                             684
```

(2) INFORMATION FOR SEQ ID NO: 35:

(i) SEQUENCE CHARACTERISTICS:
        (A) LENGTH: 614 base pairs
        (B) TYPE: nucleic acid
        (C) STRANDEDNESS: single
        (D) TOPOLOGY: linear (xi) SEQUENCE DESCRIPTION: SEQ ID NO: 35:

```
ACTAGTCCAA CGCGTTNGCN AATATTCCCC TGGTAGCCTA CTTCCTTACC CCCGAATATT       60

GGTAAGATCG AGCAATGGCT TCAGGACATG GGTTCTCTTC TCCTGTGATC ATTCAAGTGC      120

TCACTGCATG AAGACTGGCT TGTCTCAGTG TNTCAACCTC ACCAGGGCTG TCTCTTGGTC      180

CACACCTCGC TCCCTGTTAG TGCCGTATGA CAGCCCCCAT CANATGACCT TGGCCAAGTC      240

ACGGTTTCTC TGTGGTCAAT GTTGGTNGGC TGATTGGTGG AAAGTANGGT GGACCAAAGG      300

AAGNCNCGTG AGCAGNCANC NCCAGTTCTG CACCAGCAGC GCCTCCGTCC TACTNGGGTG      360

TTCCNGTTTC TCCTGGCCCT GNGTGGGCTA NGGCCTGATT CGGGAANATG CCTTTGCANG      420

GAAGGGANGA TAANTGGGAT CTACCAATTG ATTCTGGCAA AACNATNTCT AAGATTNTTN      480
```

```
TGCTTTATGT GGGANACANA TCTANCTCTC ATTTNNTGCT GNANATNACA CCCTACTCGT    540

GNTCGANCNC GTCTTCGATT TTCGGANACA CNCCANTNAA TACTGGCGTT CTGTTGTTAA    600

AAAAAAAAAA AAAA                                                       614

(2) INFORMATION FOR SEQ ID NO: 36:

(i) SEQUENCE CHARACTERISTICS:
         (A) LENGTH: 686 base pairs
         (B) TYPE: nucleic acid
         (C) STRANDEDNESS: single
         (D) TOPOLOGY: linear (xi) SEQUENCE DESCRIPTION: SEQ ID NO: 36:

GTGGCTGGCC CGGTTCTCCG CTTCTCCCCA TCCCCTACTT TCCTCCCTCC CTCCCTTTCC     60

CTCCCTCGTC GACTGTTGCT TGCTGGTCGC AGACTCCCTG ACCCCTCCCT CACCCCTCCC    120

TAACCTCGGT GCCACCGGAT TGCCCTTCTT TTCCTGTTGC CCAGCCCAGC CCTAGTGTCA    180

GGGCGGGGGC CTGGAGCAGC CCGAGGCACT GCAGCAGAAG ANANAAAAGA CACGACNAAC    240

CTCAGCTCGC CAGTCCGGTC GCTNGCTTCC CGCCGCATGG CAATNAGACA GACGCCGCTC    300

ACCTGCTCTG GCACACGCG ACCCGTGGTT GATTTGGCCT TCAGTGGCAT CACCCTTATG     360

GGTATTTCTT AATCAGCGCT TGCAAAGATG GTTAACCTAT GCTACGCCAG GGAGATACAG    420

GAGACTGGAT TGGAACATTT TTGGGGTCTA AAGGTCTGTT TGGGGTGCAA CACTGAATAA    480

GGATGCCACC AAAGCAGCTA CAGCAGCTGC AGATTTCACA GCCCAAGTGT GGGATGCTGT    540

CTCAGGANAT NAATTGATAA CCTGGCTCAT AACACATTGT CAAGAATGTG GATTTCCCCA    600

GGATATTATT ATTTGTTTAC CGGGGGANAG GATAACTGTT TCNCNTATTT TAATTGAACA    660

AACTNAAACA AAANCTAAGG AAATCC                                         686

(2) INFORMATION FOR SEQ ID NO: 37:

(i) SEQUENCE CHARACTERISTICS:
         (A) LENGTH: 681 base pairs
         (B) TYPE: nucleic acid
         (C) STRANDEDNESS: single
         (D) TOPOLOGY: linear (xi) SEQUENCE DESCRIPTION: SEQ ID NO: 37:

GAGACANACN NAACGTCANG AGAANAAAAG ANGCATGGAA CACAANCCAG GCNCGATGGC     60

CACCTTCCCA CCAGCANCCA GCGCCCCCCA GCNGCCCCCA NGCCGGANG ACCANGACTC     120

CANCCTGNAT CAATCTGANC TCTATTCCTG GCCCATNCCT ACCTCGGAGG TGGANGCCGN    180

AAAGGTCGCA CNNNCAGAGA AGCTGCTGCC ANCACCANCC GCCCCNNCCC TGNCGGGCTN    240

NATAGGAAAC TGGTGACCNN GCTGCANAAT TCATACAGGA GCACGCGANG GGCACNNNCT    300

CACACTGAGT TNNNGATGAN GCCTNACCAN GGACCTNCCC CAGCNNATTG ANNACNGGAC    360

TGCGGAGGAA GGAAGACCCC GNACNGGATC CTGGCCGGCN TGCCACCCCC CCACCCCTAG    420

GATTATNCCC CTTGACTGAG TCTCTGAGGG GCTACCCGAA CCCGCCTCCA TTCCCTACCA    480

NATNNTGCTC NATCGGGACT GACANGCTGG GGATGGAGG GGCTATCCCC CANCATCCCC    540

TNANACCAAC AGCNACNGAN NATNGGGGCT CCCCNGGGTC GGNGCAACNC TCCTNCACCC    600

CGGCGCNGGC CTTCGGTGNT GTCCTCCNTC AACNAATTCC NAAANGGCGG GCCCCCCNGT    660

GGACTCCTCN TTGTTCCCTC C                                              681

(2) INFORMATION FOR SEQ ID NO: 38:
```

(i) SEQUENCE CHARACTERISTICS:
    (A) LENGTH: 687 base pairs
    (B) TYPE: nucleic acid
    (C) STRANDEDNESS: single
    (D) TOPOLOGY: linear (xi) SEQUENCE DESCRIPTION: SEQ ID NO: 38:

| | | | | | |
|---|---|---|---|---|---|
| CANAAAAAAA | AAAACATGGC | CGAAACCAGN | AAGCTGCGCG | ATGGCGCCAC | GGCCCCTCTT | 60 |
| CTCCCGGCCT | GTGTCCGGAA | GGTTTCCCTC | CGAGGCGCCC | CGGCTCCCGC | AAGCGGAGGA | 120 |
| GAGGGCGGGA | CNTGCCGGGG | CCGGAGCTCA | NAGGCCCTGG | GGCCGCTCTG | CTCTCCCGCC | 180 |
| ATCGCAAGGG | CGGCGCTAAC | CTNAGGCCTC | CCCGCAAAGG | TCCCCNANGC | GGNGGCGGCG | 240 |
| GGGGGCTGTG | ANAACCGCAA | AAANAACGCT | GGGCGCGCNG | CGAACCCGTC | CACCCCCGCG | 300 |
| AAGGANANAC | TTCCACAGAN | GCAGCGTTTC | CACAGCCCAN | AGCCACNTTT | CTAGGGTGAT | 360 |
| GCACCCCAGT | AAGTTCCTGN | CGGGGAAGCT | CACCGCTGTC | AAAAAANCTC | TTCGCTCCAC | 420 |
| CGGCGCACNA | AGGGGANGAN | GGCANGANGC | TGCCGCCCGC | ACAGGTCATC | TGATCACGTC | 480 |
| GCCCGCCCTA | NTCTGCTTTT | GTGAATCTCC | ACTTTGTTCA | ACCCCACCCG | CCGTTCTCTC | 540 |
| CTCCTTGCGC | CTTCCTCTNA | CCTTAANAAC | CAGCTTCCTC | TACCCNATNG | TANTTNCTCT | 600 |
| GCNCNNGTNG | AAATTAATTC | GGTCCNCCGG | AACCTCTTNC | CTGTGGCAAC | TGCTNAAAGA | 660 |
| AACTGCTGTT | CTGNTTACTG | CNGTCCC | | | | 687 |

(2) INFORMATION FOR SEQ ID NO: 39:

(i) SEQUENCE CHARACTERISTICS:
        (A) LENGTH: 695 base pairs
        (B) TYPE: nucleic acid
        (C) STRANDEDNESS: single
        (D) TOPOLOGY: linear (xi) SEQUENCE DESCRIPTION: SEQ ID NO: 39:

| | | | | | |
|---|---|---|---|---|---|
| ACTAGTCTGG | CCTACAATAG | TGTGATTCAT | GTAGGACTTC | TTTCATCAAT | TCAAAACCCC | 60 |
| TAGAAAAACG | TATACAGATT | ATATAAGTAG | GGATAAGATT | TCTAACATTT | CTGGGCTCTC | 120 |
| TGACCCCTGC | GCTAGACTGT | GGAAAGGGAG | TATTATTATA | GTATACAACA | CTGCTGTTGC | 180 |
| CTTATTAGTT | ATAACATGAT | AGGTGCTGAA | TTGTGATTCA | CAATTTAAAA | ACACTGTAAT | 240 |
| CCAAACTTTT | TTTTTTAACT | GTAGATCATG | CATGTGAATG | TTAATGTTAA | TTTGTTCAAN | 300 |
| GTTGTTATGG | GTAGAAAAAA | CCACATGCCT | TAAAATTTTA | AAAAGCAGGG | CCCAAACTTA | 360 |
| TTAGTTTAAA | ATTAGGGGTA | TGTTTCCAGT | TTGTTATTAA | NTGGTTATAG | CTCTGTTTAG | 420 |
| AANAAATCNA | NGAACANGAT | TTNGAAANTT | AAGNTGACAT | TATTTNCCAG | TGACTTGTTA | 480 |
| ATTTGAAATC | ANACACGGCA | CCTTCCGTTT | TGGTNCTATT | GGNNTTTGAA | TCCAANCNGG | 540 |
| NTCCAAATCT | TNTTGGAAAC | NGTCCNTTTA | ACTTTTTTAC | NANATCTTAT | TTTTTTATTT | 600 |
| TGGAATGGCC | CTATTTAANG | TTAAAAGGGG | GGGGNNCCAC | NACCATTCNT | GAATAAAACT | 660 |
| NAATATATAT | CCTTGGTCCC | CCAAAATTTA | AGGNG | | | 695 |

(2) INFORMATION FOR SEQ ID NO: 40:

(i) SEQUENCE CHARACTERISTICS:
        (A) LENGTH: 674 base pairs
        (B) TYPE: nucleic acid
        (C) STRANDEDNESS: single
        (D) TOPOLOGY: linear (xi) SEQUENCE DESCRIPTION: SEQ ID NO: 40:

| | | | | | |
|---|---|---|---|---|---|
| ACTAGTAGTC | AGTTGGGAGT | GGTTGCTATA | CCTTGACTTC | ATTTATATGA | ATTTCCACTT | 60 |

```
TATTAAATAA TAGAAAAGAA AATCCCGGTG CTTGCAGTAG AGTTATAGGA CATTCTATGC      120

TTACAGAAAA TATAGCCATG ATTGAAATCA AATAGTAAAG GCTGTTCTGG CTTTTTATCT      180

TCTTAGCTCA TCTTAAATAA GTAGTACACT TGGGATGCAG TGCGTCTGAA GTGCTAATCA      240

GTTGTAACAA TAGCACAAAT CGAACTTAGG ATGTGTTTCT TCTCTTCTGT GTTTCGATTT      300

TGATCAATTC TTTAATTTTG GGAACCTATA ATACAGTTTT CCTATTCTTG GAGATAAAAA      360

TTAAATGGAT CACTGATATT TAAGTCATTC TGCTTCTCAT CTNAATATTC CATATTCTGT      420

ATTAGGANAA ANTACCTCCC AGCACAGCCC CCTCTCAAAC CCCACCCAAA ACCAAGCATT      480

TGGAATGAGT CTCCTTTATT TCCGAANTGT GGATGGTATA ACCCATATCN CTCCAATTTC      540

TGNTTGGGTT GGGTATTAAT TTGAACTGTG CATGAAAAGN GGNAATCTTT NCTTTGGGTC      600

AAANTTTNCC GGTTAATTTG NCTNGNCAAA TCCAATTTNC TTTAAGGGTG TCTTTATAAA      660

ATTTGCTATT CNGG                                                        674

(2) INFORMATION FOR SEQ ID NO: 41:

(i) SEQUENCE CHARACTERISTICS:
        (A) LENGTH: 657 base pairs
        (B) TYPE: nucleic acid
        (C) STRANDEDNESS: single
        (D) TOPOLOGY: linear (xi) SEQUENCE DESCRIPTION: SEQ ID NO:41:

GAAACATGCA AGTACCACAC ACTGTTTGAA TTTTGCACAA AAAGTGACTG TAGGGATCAG       60

GTGATAGCCC CGGAATGTAC AGTGTCTTGG TGCACCAAGA TGCCTTCTAA AGGCTGACAT      120

ACCTTGGGAC CCTAATGGGG CAGAGAGTAT AGCCCTAGCC CAGTGGTGAC ATGACCACTC      180

CCTTTGGGAG GCTGAAGTTA AAGGGAATGG TATGTGTTTT CTCATGGAAG CAGCACATGA      240

ATNGGTNACA NGATGTTAAA NTAAGGNTCT ANTTTGGGTG TCTTGTCATT TGAAAAANTG      300

ACACACTCCT ANCANCTGGT AAAGGGGTGC TGGAAGCCAT GGAAGAACTC TAAAAACATT      360

AGCATGGGCT GATCTGATTA CTTCCTGGCA TCCCGCTCAC TTTTATGGGA AGTCTTATTA      420

NAAGGATGGG ANANTTTTCC ATATCCTTGC TGTTGGAACT CTGGAACACT CTCTAAATTT      480

CCCTCTATTA AAAATCACTG NCCTTACTAC ACTTCCTCCT TGANGGAATA GAAATGGACC      540

TTTCTCTGAC TTAGTTCTTG GCATGGGANC CAGCCCAAAT TAAAATCTGA CTTNTCCGGT      600

TTCTCCNGAA CTCACCTACT TGAATTGGTA AAACCTCCTT TGGAATTAGN AAAAACC        657

(2) INFORMATION FOR SEQ ID NO: 42:

(i) SEQUENCE CHARACTERISTICS:
        (A) LENGTH: 389 base pairs
        (B) TYPE: nucleic acid
        (C) STRANDEDNESS: single
        (D) TOPOLOGY: linear (xi) SEQUENCE DESCRIPTION: SEQ ID NO: 42:

ACTAGTGCTG AGGAATGTAA ACAAGTTTGC TGGGCCTTGC GAGACTTCAC CAGGTTGTTT       60

CGATAGCTCA CACTCCTGCA CTGTGCCTGT CACCCAGGAA TGTCTTTTTT AATTAGAAGA      120

CAGGAAGAAA ACAAAAACCA GACTGTGTCC CACAATCAGA AACCTCCGTT GTGGCAGANG      180

GGCCTTCACC GCCACCAGGG TGTCCCGCCA GACAGGGAGA GACTCCAGCC TTCTGAGGCC      240

ATCCTGAAGA ATTCCTGTTT GGGGGTTGTG AAGGAAAATC ACCCGGATTT AAAAAGATGC      300

TGTTGCCTGC CCGCGTNGTN GGGAAGGGAC TGGTTTCCTG GTGAATTTCT TAAAAGAAAA      360
```

```
ATATTTTAAG TTAAGAAAAA AAAAAAAAA                                              389

(2) INFORMATION FOR SEQ ID NO: 43:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (xi) SEQUENCE DESCRIPTION: SEQ ID NO: 43:

ACTAGTGACA AGCTCCTGGT CTTGAGATGT CTTCTCGTTA AGGAGATGGG CCTTTTGGAG            60

GTAAAGGATA AAATGAATGA GTTCTGTCAT GATTCACTAT TCTAGAACTT GCATGACCTT           120

TACTGTGTTA GCTCTTTGAA TGTTCTTGAA ATTTTAGACT TTCTTTGTAA ACAAATAATA           180

TGTCCTTATC ATTGTATAAA AGCTGTTATG TGCAACAGTG TGGAGATCCT TGTCTGATTT           240

AATAAAATAC TTAAACACTG AAAAAAAAAA AAAAAAAA                                   279

(2) INFORMATION FOR SEQ ID NO: 44:

(i) SEQUENCE CHARACTERISTICS:
        (A) LENGTH: 449 base pairs
        (B) TYPE: nucleic acid
        (C) STRANDEDNESS: single
        (D) TOPOLOGY: linear (xi) SEQUENCE DESCRIPTION: SEQ ID NO: 44:

ACTAGTAGCA TCTTTTCTAC AACGTTAAAA TTGCAGAAGT AGCTTATCAT TAAAAAACAA            60

CAACAACAAC AATAACAATA AATCCTAAGT GTAAATCAGT TATTCTACCC CCTACCAAGG           120

ATATCAGCCT GTTTTTTCCC TTTTTTCTCC TGGGAATAAT TGTGGGCTTC TTCCCAAATT           180

TCTACAGCCT CTTTCCTCTT CTCATGCTTG AGCTTCCCTG TTTGCACGCA TGCGTTGTGC           240

AAGANTGGGC TGTTTNGCTT GGANTNCGGT CCNAGTGGAA NCATGCTTTC CCTTGTTACT           300

GTTGGAAGAA ACTCAAACCT TCNANCCCTA GGTGTTNCCA TTTTGTCAAG TCATCACTGT           360

ATTTTTGTAC TGGCATTAAC AAAAAAAGAA ATNAAATATT GTTCCATTAA ACTTTAATAA           420

AACTTTAAAA GGGAAAAAAA AAAAAAAA                                              449

(2) INFORMATION FOR SEQ ID NO: 45:

(i) SEQUENCE CHARACTERISTICS:
        (A) LENGTH: 559 base pairs
        (B) TYPE: nucleic acid
        (C) STRANDEDNESS: single
        (D) TOPOLOGY: linear (xi) SEQUENCE DESCRIPTION: SEQ ID NO: 45:

ACTAGTGTGG GGGAATCACG GACACTTAAA GTCAATCTGC GAAATAATTC TTTTATTACA            60

CACTCACTGA AGTTTTTGAG TCCCAGAGAG CCATTCTATG TCAAACATTC CAAGTACTCT           120

TTGAGAGCCC AGCATTACAT CAACATGCCC GTGCAGTTCA AACCGAAGTC CGCAGGCAAA           180

TTTGAAGCTT TGCTTGTCAT TCAAACAGAT GAAGGCAAGA GTATTGCTAT TCGACTAATT           240

GGTGAAGCTC TTGGAAAAAA TTNACTAGAA TACTTTTTGT GTTAAGTTAA TTACATAAGT           300

TGTATTTTGT TAACTTTATC TTTCTACACT ACAATTATGC TTTTGTATAT ATATTTTGTA           360

TGATGGATAT CTATAATTGT AGATTTTGTT TTTACAAGCT AATACTGAAG ACTCGACTGA           420

AATATTATGT ATCTAGCCCA TAGTATTGTA CTTAACTTTT ACAGGGTGAA AAAAAAATTC           480

TGTGTTTGCA TTGATTATGA TATTCTGAAT AAATATGGGA ATATATTTTA ATGTGGGTAA           540
```

AAAAAAAAAA AAAAAGGAA                                              559

(2) INFORMATION FOR SEQ ID NO: 46:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (xi) SEQUENCE DESCRIPTION: SEQ ID NO: 46:

ACTAGTTCTA GTACCATGGC TGTCATAGAT GCAACCATTA TATTCCATTT AGTTTCTTCC    60

TCAGGTTCCC TAACAATTGT TTGAAACTGA ATATATATGT TTATGTATGT GTGTGTGTTC   120

ACTGTCATGT ATATGGTGTA TATGGGATGT GTGCAGTTTT CAGTTATATA TATATTCATA   180

TATACATATG CATATATATG TATAATATAC ATATATACAT GCATACACTT GTATAATATA   240

CATATATATA CACATATATG CACACATATN ATCACTGAGT TCCAAAGTGA GTCTTTATTT   300

GGGGCAATTG TATTCTCTCC CTCTGTCTGC TCACTGGGCC TTTGCAAGAC ATAGCAATTG   360

CTTGATTTCC TTTGGATAAG AGTCTTATCT TCGGCACTCT TGACTCTAGC CTTAACTTTA   420

GATTTCTATT CCAGAATACC TCTCATATCT ATCTTAAAAC CTAAGANGGG TAAAGANGTC   480

ATAAGATTGT AGTATGAAAG ANTTTGCTTA GTTAAATTAT ATCTCAGGAA ACTCATTCAT   540

CTACAAATTA AATTGTAAAA TGATGGTTTG TTGTATCTGA AAAAATGTTT AGAACAAGAA   600

ATGTAACTGG GTACCTGTTA TATCAAAGAA CCTCNATTTA TTAAGTCTCC TCATAGCCAN   660

ATCCTTATAT NGCCCTCTCT GACCTGANTT AATANANACT TGAATAATGA ATAGTTAATT   720

TAGGNTTGGG C                                                      731

(2) INFORMATION FOR SEQ ID NO: 47:

(i) SEQUENCE CHARACTERISTICS:
        (A) LENGTH: 640 base pairs
        (B) TYPE: nucleic acid
        (C) STRANDEDNESS: single
        (D) TOPOLOGY: linear (xi) SEQUENCE DESCRIPTION: SEQ ID NO: 47:

TGCGNGCCGG TTTGGCCCTT CTTTGTANGA CACTTTCATC CGCCCTGAAA TCTTCCCGAT    60

CGTTAATAAC TCCTCAGGTC CCTGCCTGCA CAGGGTTTTT TCTTANTTTG TTGCCTAACA   120

GTACACCAAA TGTGACATCC TTTCACCAAT ATNGATTNCT TCATACCACA TCNTCNATGG   180

ANACGACTNC AACAATTTTT TGATNACCCN AAANACTGGG GGCTNNAANA AGTACANTCT   240

GGAGCAGCAT GGACCTGTCN GCNACTAANG GAACAANAGT NNTGAACATT TACACAACCT   300

TTGGTATGTC TTACTGAAAG ANAGAAACAT GCTTCTNNCC CTAGACCACG AGGNCAACCG   360

CAGANATTGC CAATGCCAAG TCCGAGCGGT TAGATCAGGT AATACATTCC ATGGATGCAT   420

TACATACNTT GTCCCCGAAA NANAAGATGC CCTAANGGCT TCTTCANACT GGTCCNGAAA   480

ACANCTACAC CTGGTGCTTG GANAACANAC TCTTTGGAAG ATCATCTGGC ACAAGTTCCC   540

CCCAGTGGGT TTTNCCTTGG CACCTANCTT ACCANATCNA TTCGGAANCC ATTCTTTGCC   600

NTGGCNTTNT NTTGGGACCA NTCTTCTCAC AACTGNACCC                        640

(2) INFORMATION FOR SEQ ID NO: 48:

(i) SEQUENCE CHARACTERISTICS:
        (A) LENGTH: 257 base pairs
        (B) TYPE: nucleic acid
        (C) STRANDEDNESS: single (D) TOPOLOGY: linear (xi) SEQUENCE DESCRIPTION: SEQ ID NO: 48:

ACTAGTATAT GAAAATGTAA ATATCACTTG TGTACTCAAA CAAAAGTTGG TCTTAAGCTT      60

CCACCTTGAG CAGCCTTGGA AACCTAACCT GCCTCTTTTA GCATAATCAC ATTTTCTAAA     120

TGATTTTCTT TGTTCCTGAA AAAGTGATTT GTATTAGTTT TACATTTGTT TTTTGGAAGA     180

TTATATTTGT ATATGTATCA TCATAAAATA TTTAAATAAA AAGTATCTTT AGAGTGAAAA     240

AAAAAAAAAA AAAAAAA                                                   257

(2) INFORMATION FOR SEQ ID NO: 49:

(i) SEQUENCE CHARACTERISTICS:
        (A) LENGTH: 652 base pairs
        (B) TYPE: nucleic acid
        (C) STRANDEDNESS: single
        (D) TOPOLOGY: linear (xi) SEQUENCE DESCRIPTION: SEQ ID NO: 49:

ACTAGTTCAG ATGAGTGGCT GCTGAAGGGG CCCCCTTGTC ATTTTCATTA TAACCCAATT      60

TCCACTTATT TGAACTCTTA AGTCATAAAT GTATAATGAC TTATGAATTA GCACAGTTAA     120

GTTGACACTA GAAACTGCCC ATTTCTGTAT TACACTATCA AATAGGAAAC ATTGGAAAGA     180

TGGGGAAAAA AATCTTATTT TAAAATGGCT TAGAAAGTTT TCAGATTACT TTGAAAATTC     240

TAAACTTCTT TCTGTTTCCA AAACTTGAAA ATATGTAGAT GGACTCATGC ATTAAGACTG     300

TTTTCAAAGC TTTCCTCACA TTTTTAAAGT GTGATTTTCC TTTTAATATA CATATTTATT     360

TTCTTTAAAG CAGCTATATC CCAACCCATG ACTTTGGAGA TATACCTATN AAACCAATAT     420

AACAGCANGG TTATTGAAGC AGCTTTCTCA ATGTTGCTT CAGATGTGCA AGTTGCAAAT      480

TTTATTGTAT TTGTANAATA CAATTTTTGT TTTAAACTGT ATTTCAATCT ATTTCTCCAA     540

GATGCTTTTC ATATAGAGTG AAATATCCCA NGATAACTGC TTCTGTGTCG TCGCATTTGA     600

CGCATAACTG CACAAATGAA CAGTGTATAC CTCTTGGTTG TGCATTNACC CC            652

(2) INFORMATION FOR SEQ ID NO: 50:

(i) SEQUENCE CHARACTERISTICS:
        (A) LENGTH: 650 base pairs
        (B) TYPE: nucleic acid
        (C) STRANDEDNESS: single
        (D) TOPOLOGY: linear (xi) SEQUENCE DESCRIPTION: SEQ ID NO: 50:

TTGCGCTTTG ATTTTTTTAG GGCTTGTGCC CTGTTTCACT TATAGGGTCT AGAATGCTTG      60

TGTTGAGTAA AAAGGAGATG CCCAATATTC AAAGCTGCTA AATGTTCTCT TGCCATAAA     120

GACTCCGTGT AACTGTGTGA ACACTTGGGA TTTTTCTCCT CTGTCCCGAG GTCGTCGTCT     180

GCTTTCTTTT TTGGGTTCTT TCTAGAAGAT TGAGAAATGC ATATGACAGG CTGAGANCAC     240

CTCCCCAAAC ACACAAGCTC TCAGCCACAN GCAGCTTCTC CACAGCCCCA GCTTCGCACA     300

GGCTCCTGGA NGGCTGCCTG GGGGAGGCAG ACATGGGAGT GCCAAGGTGG CCAGATGGTT     360

CCAGGACTAC AATGTCTTTA TTTTTAACTG TTTGCCACTG CTGCCCTCAC CCCTGCCCGG     420

CTCTGGAGTA CCGTCTGCCC CANACAAGTG GGANTGAAAT GGGGGTGGGG GGGAACACTG     480

ATTCCCANTT AGGGGGTGCC TAACTGAACA GTAGGGATAN AAGGTGTGAA CCTGNGAANT     540

GCTTTTATAA ATTATNTTCC TTGTTANATT TATTTTTTAA TTTAATCTCT GTTNAACTGC     600

CCNGGGAAAA GGGGAAAAAA AAAAAAAAAT TCTNTTTAAA CACATGAACA                650

(2) INFORMATION FOR SEQ ID NO: 51:

(i) SEQUENCE CHARACTERISTICS:
        (A) LENGTH: 545 base pairs
        (B) TYPE: nucleic acid
        (C) STRANDEDNESS: single
        (D) TOPOLOGY: linear (xi) SEQUENCE DESCRIPTION: SEQ ID NO: 51:

```
TGGCGTGCAA CCAGGGTAGC TGAAGTTTGG GTCTGGGACT GGAGATTGGC CATTAGGCCT      60
CCTGANATTC CAGCTCCCTT CCACCAAGCC CAGTCTTGCT ACGTGGCACA GGGCAAACCT     120
GACTCCCTTT GGGCCTCAGT TTCCCCTCCC CTTCATGANA TGAAAAGAAT ACTACTTTTT     180
CTTGTTGGTC TAACNTTGCT GGACNCAAAG TGTNGTCATT ATTGTTGTAT TGGGTGATGT     240
GTNCAAAACT GCAGAAGCTC ACTGCCTATG AGAGGAANTA AGAGAGATAG TGGATGANAG     300
GGACANAAGG AGTCATTATT TGGTATAGAT CCACCCNTCC CAACCTTTCT CTCCTCAGTC     360
CCTGCNCCTC ATGTNTCTGG TNTGGTGAGT CCTTTGTGCC ACCANCCATC ATGCTTTGCA     420
TTGCTGCCAT CCTGGGAAGG GGGTGNATCG TCTCACAACT TGTTGTCATC GTTTGANATG     480
CATGCTTTCT TNATNAAACA AANAAANNAA TGTTTGACAG NGTTTAAAAT AAAAAANAAA     540
CAAAA                                                                545
```

(2) INFORMATION FOR SEQ ID NO: 52:

(i) SEQUENCE CHARACTERISTICS:
        (A) LENGTH: 678 base pairs
        (B) TYPE: nucleic acid
        (C) STRANDEDNESS: single
        (D) TOPOLOGY: linear (xi) SEQUENCE DESCRIPTION: SEQ ID NO: 52:

```
ACTAGTAGAA GAACTTTGCC GCTTTTGTGC CTCTCACAGG CGCCTAAAGT CATTGCCATG      60
GGAGGAAGAC GATTTGGGGG GGGAGGGGGG GGGGGCANGG TCCGTGGGGC TTTCCCTANT     120
NTATCTCCAT NTCCANTGNN CNNTGTCGCC TCTTCCCTCG TCNCATTNGA ANTTANTCCC     180
TGGNCCCCNN NCCCTCTCCN NCCTNCNCCT CCCCCCTCCG NCNCCTCCNN CTTTTTNTAN     240
NCTTCCCCAT CTCCNTCCCC CCTNANNGTC CCAACNCCGN CAGCAATNNC NCACTTNCTC     300
NCTCCNCNCC TCCNNCCGTT CTTCTNTTCT CNACNTNTNC NCNNNTNCCN TGCCNNTNAA     360
ANNCTCTCCC CNCTGCAANC GATTCTCTCC CTCCNCNNAN CTNTCCACTC CNTNCTTCTC     420
NCNCGCTCCT NTTCNTCNNC CCACCTCTCN CCTTCGNCCC CANTACNCTC NCCNCCCTTN     480
CGNNTCNTTN NNNTCCTCNN ACCNCCCNCC TCCCTTCNCC CCTCTTCTCC CCGGTNTNTC     540
TCTCTCCCNC NNCNCNNCCT CNNCCCNTCC NNGCGNCCNT TTCCGCCCCN CNCCNCCNTT     600
CCTTCNTCNC CANTCCATCN CNTNTNCCAT NCTNCCTNCC NCTCACNCCC GCTNCCCCCN     660
NTCTCTTTCA CACNGTCC                                                  678
```

(2) INFORMATION FOR SEQ ID NO: 53:

(i) SEQUENCE CHARACTERISTICS:
        (A) LENGTH: 502 base pairs
        (B) TYPE: nucleic acid
        (C) STRANDEDNESS: single
        (D) TOPOLOGY: linear (xi) SEQUENCE DESCRIPTION: SEQ ID NO: 53:

```
TGAAGATCCT GGTGTCGCCA TGGGCCGCCG CCCCGCCCGT TGTTACCGGT ATTGTAAGAA      60
```

```
CAAGCCGTAC CCAAAGTCTC GCTTCTGCCG AGGTGTCCCT GATGCCAAAA TTCGCATTTT      120

TGACCTGGGG CGGAAAAANG CAAAANTGGA TGAGTCTCCG CTTTGTGGCC ACATGGTGTC      180

AGATCAATAT GAGCAGCTGT CCTCTGAAGC CCTGNANGCT GCCCGAATTT GTGCCAATAA      240

GTACATGGTA AAAAGTNGTG GCNAAGATGC TTCCATATCC GGGTGCGGNT CCACCCCTTC      300

CACGTCATCC GCATCAACAA GATGTTGTCC TGTGCTGGGG CTGACAGGCT CCCAACAGGC      360

ATGCGAAGTG CCTTTGGAAA ACCCANGGCA CTGTGGCCAG GGTTCACATT GGGCCAATTN      420

ATCATGTTCA TCCGCACCAA CTGCAGAACA ANGAACNTGT NAATTNAAGC CCTGCCCAGG      480

GNCAANTTCA AATTTCCCGG CC                                              502

(2) INFORMATION FOR SEQ ID NO: 54:

(i) SEQUENCE CHARACTERISTICS:
        (A) LENGTH: 494 base pairs
        (B) TYPE: nucleic acid
        (C) STRANDEDNESS: single
        (D) TOPOLOGY: linear (xi) SEQUENCE DESCRIPTION: SEQ ID NO: 54:

ACTAGTCCAA GAAAAATATG CTTAATGTAT ATTACAAAGG CTTTGTATAT GTTAACCTGT       60

TTTAATGCCA AAAGTTTGCT TGTCCACAA TTTCCTTAAG ACCTCTTCAG AAAGGGATTT      120

GTTTGCCTTA ATGAATACTG TTGGGAAAAA ACACAGTATA ATGAGTGAAA AGGGCAGAAG      180

CAAGAAATTT CTACATCTTA GCGACTCCAA GAAGAATGAG TATCCACATT TAGATGGCAC      240

ATTATGAGGA CTTTAATCTT TCCTTAAACA CAATAATGTT TTCTTTTTTC TTTTATTCAC      300

ATGATTTCTA AGTATATTTT TCATGCAGGA CAGTTTTTCA ACCTTGATGT ACAGTGACTG      360

TGTTAAATTT TTCTTTCAGT GGCAACCTCT ATAATCTTTA AAATATGGTG AGCATCTTGT      420

CTGTTTTGAA NGGGATATGA CNATNAATCT ATCAGATGGG AAATCCTGTT TCCAAGTTAG      480

AAAAAAAAAA AAAA                                                       494

(2) INFORMATION FOR SEQ ID NO: 55:

(i) SEQUENCE CHARACTERISTICS:
        (A) LENGTH: 606 base pairs
        (B) TYPE: nucleic acid
        (C) STRANDEDNESS: single
        (D) TOPOLOGY: linear (xi) SEQUENCE DESCRIPTION: SEQ ID NO: 55:

ACTAGTAAAA AGCAGCATTG CCAAATAATC CCTAATTTTC CACTAAAAAT ATAATGAAAT       60

GATGTTAAGC TTTTTGAAAA GTTTAGGTTA AACCTACTGT TGTTAGATTA ATGTATTTGT      120

TGCTTCCCTT TATCTGGAAT GTGGCATTAG CTTTTTTATT TTAACCCTCT TTAATTCTTA      180

TTCAATTCCA TGACTTAAGG TTGGAGAGCT AAACACTGGG ATTTTTGGAT AACAGACTGA      240

CAGTTTTGCA TAATTATAAT CGGCATTGTA CATAGAAAGG ATATGGCTAC CTTTTGTTAA      300

ATCTGCACTT TCTAAATATC AAAAAAGGGA AATGAAGTAT AAATCAATTT TTGTATAATC      360

TGTTTGAAAC ATGANTTTTA TTTGCTTAAT ATTANGGCTT TGCCCTTTTC TGTTAGTCTC      420

TTGGGATCCT GTGTAAAACT GTTCTCATTA AACACCAAAC AGTTAAGTCC ATTCTCTGGT      480

ACTAGCTACA AATTCCGTTT CATATTCTAC NTAACAATTT AAATTAACTG AAATATTTCT      540

ANATGGTCTA CTTCTGTCNT ATAAAAACNA AACTTGANTT NCCAAAAAAA AAAAAAAAA      600

AAAAAA                                                                606
```

(2) INFORMATION FOR SEQ ID NO: 56:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (xi) SEQUENCE DESCRIPTION: SEQ ID NO: 56:

```
ACTAGTATAT TTAAACTTAC AGGCTTATTT GTAATGTAAA CCACCATTTT AATGTACTGT      60

AATTAACATG TTATAATAC GTACAATCCT TCCCTCATCC CATCACACAA CTTTTTTTGT     120

GTGTGATAAA CTGATTTTGG TTTGCAATAA AACCTTGAAA ATAAAAAAAA AAAAAAAAA     180

AAA                                                                  183
```

(2) INFORMATION FOR SEQ ID NO: 57:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (xi) SEQUENCE DESCRIPTION: SEQ ID NO: 57:

```
ACTAGTCACT ACTGTCTTCT CCTTGTAGCT AATCAATCAA TATTCTTCCC TTGCCTGTGG      60

GCAGTGGAGA GTGCTGCTGG GTGTACGCTG CACCTGCCCA CTGAGTTGGG GAAAGAGGAT     120

AATCAGTGAG CACTGTTCTG CTCAGAGCTC CTGATCTACC CCACCCCCTA GGATCCAGGA     180

CTGGGTCAAA GCTGCATGAA ACCAGGCCCT GGCAGCAACC TGGGAATGGC TGGAGGTGGG     240

AGAGAACCTG ACTTCTCTTT CCCTCTCCCT CCTCCAACAT TACTGGAACT CTATCCTGTT     300

AGGGATCTTC TGAGCTTGTT TCCCTGCTGG GTGGGACAGA AGACAAAGGA GAAGGGANGG     360

TCTACAANAA GCAGCCCTTC TTTGTCCTCT GGGGTTAATG AGCTTGACCT ANANTTCATG     420

GAGANACCAN AAGCCTCTGA TTTTTAATTT CCNTNAAATG TTTGAAGTNT ATATNTACAT     480

ATATATATTT CTTTNAATNT TTGAGTCTTT GATATGTCTT AAAATCCANT CCCTCTGCCN     540

GAAACCTGAA TTAAAACCAT GAANAAAAAT GTTTNCCTTA AGATGTTAN TAATTAATTG     600

AAACTTGAAA AAAAAAAAA AA                                              622
```

(2) INFORMATION FOR SEQ ID NO: 58:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (xi) SEQUENCE DESCRIPTION: SEQ ID NO: 58:

```
GAACAAATTC TGATTGGTTA TGTACCGTCA AAAGACTTGA AGAAATTTCA TGATTTTGCA      60

GTGTGGAAGC GTTGAAAATT GAAAGTTACT GCTTTTCCAC TTGCTCATAT AGTAAAGGGA     120

TCCTTTCAGC TGCCAGTGTT GAATAATGTA TCATCCAGAG TGATGTTATC TGTGACAGTC     180

ACCAGCTTTA AGCTGAACCA TTTTATGAAT ACCAAATAAA TAGACCTCTT GTACTGAAAA     240

CATATTTGTG ACTTTAATCG TGCTGCTTGG ATAGAAATAT TTTTACTGGT TCTTCTGAAT     300

TGACAGTAAA CCTGTCCATT ATGAATGGCC TACTGTTCTA TTATTTGTTT TGACTTGAAT     360

TTATCCACCA AAGACTTCAT TTGTGTATCA TCAATAAAGT TGTATGTTTC AACTGAAAAA     420

AAAAAAAAA AAA                                                        433
```

(2) INFORMATION FOR SEQ ID NO: 59:

(i) SEQUENCE CHARACTERISTICS:
       (A) LENGTH: 649 base pairs
       (B) TYPE: nucleic acid
       (C) STRANDEDNESS: single
       (D) TOPOLOGY: linear (xi) SEQUENCE DESCRIPTION: SEQ ID NO: 59:

| | | | | | |
|---|---|---|---|---|---|
| ACTAGTTATT | ATCTGACTTT | CNGGTTATAA | TCATTCTAAT | GAGTGTGAAG | TAGCCTCTGG | 60 |
| TGTCATTTGG | ATTTGCATTT | CTCTGATGAG | TGATGCTATC | AAGCACCTTT | GCTGGTGCTG | 120 |
| TTGGCCATAT | GTGTATGTTC | CCTGGAGAAG | TGTCTGTGCT | GAGCCTTGGC | CCACTTTTTA | 180 |
| ATTAGGCGTN | TGTCTTTTTA | TTACTGAGTT | GTAAGANTTC | TTTATATATT | CTGGATTCTA | 240 |
| GACCCTTATC | AGATACATGG | TTTGCAAATA | TTTTCTCCCA | TTCTGTGGGT | TGTGTTTTCA | 300 |
| CTTTATCGAT | AATGTCCTTA | GACATATAAT | AAATTTGTAT | TTTAAAAGTG | ACTTGATTTG | 360 |
| GGCTGTGCAA | GGTGGGCTCA | CGCTTGTAAT | CCCAGCACTT | TGGGAGACTG | AGGTGGGTGG | 420 |
| ATCATATGAN | GANGCTAGGA | GTTCGAGGTC | AGCCTGGCCA | GCATAGCGAA | AACTTGTCTC | 480 |
| TACNAAAAAT | ACAAAAATTA | GTCAGGCATG | GTGGTGCACG | TCTGTAATAC | CAGCTTCTCA | 540 |
| GGANGCTGAN | GCACAAGGAT | CACTTGAACC | CCAGAANGAA | GANGTTGCAG | TGANCTGAAG | 600 |
| ATCATGCCAG | GGCAACAAAA | ATGAGAACTT | GTTTAAAAAA | AAAAAAAA | | 649 |

(2) INFORMATION FOR SEQ ID NO: 60:

(i) SEQUENCE CHARACTERISTICS:
       (A) LENGTH: 423 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO: 60:

| | | | | | |
|---|---|---|---|---|---|
| ACTAGTTCAG | GCCTTCCAGT | TCACTGACAA | ACATGGGGAA | GTGTGCCCAG | CTGGCTGGAA | 60 |
| ACCTGGCAGT | GATACCATCA | AGCCTGATGT | CCAAAAGAGC | AAAGAATATT | TCTCCAAGCA | 120 |
| GAAGTGAGCG | CTGGGCTGTT | TTAGTGCCAG | GCTGCGGTGG | GCAGCCATGA | GAACAAAACC | 180 |
| TCTTCTGTAT | TTTTTTTTTC | CATTAGTANA | ACACAAGACT | CNGATTCAGC | CGAATTGTGG | 240 |
| TGTCTTACAA | GGCAGGGCTT | TCCTACAGGG | GGTGGANAAA | ACAGCCTTTC | TTCCTTTGGT | 300 |
| AGGAATGGCC | TGAGTTGGCG | TTGTGGGCAG | GCTACTGGTT | TGTATGATGT | ATTAGTAGAG | 360 |
| CAACCCATTA | ATCTTTTGTA | GTTTGTATNA | AACTTGANCT | GAGACCTTAA | ACAAAAAAAA | 420 |
| AAA | | | | | | 423 |

(2) INFORMATION FOR SEQ ID NO: 61:

(i) SEQUENCE CHARACTERISTICS:
       (A) LENGTH: 423 base pairs
       (B) TYPE: nucleic acid
       (C) STRANDEDNESS: single
       (D) TOPOLOGY: linear (xi) SEQUENCE DESCRIPTION: SEQ ID NO: 61:

| | | | | | |
|---|---|---|---|---|---|
| CGGGACTGGA | ATGTAAAGTG | AAGTTCGGAG | CTCTGAGCAC | GGGCTCTTCC | CGCCGGGTCC | 60 |
| TCCCTCCCCA | GACCCCAGAG | GGAGAGGCCC | ACCCCGCCCA | GCCCCGCCCC | AGCCCCTGCT | 120 |
| CAGGTCTGAG | TATGGCTGGG | AGTCGGGGGC | CACAGGCCTC | TAGCTGTGCT | GCTCAAGAAG | 180 |

```
ACTGGATCAG GGTANCTACA AGTGGCCGGG CCTTGCCTTT GGGATTCTAC CCTGTTCCTA      240

ATTTGGTGTT GGGGTGCGGG GTCCCTGGCC CCCTTTTCCA CACTNCCTCC CTCCNGACAG      300

CAACCTCCCT TGGGGCAATT GGGCCTGGNT CTCCNCCCGN TGTTGCNACC CTTTGTTGGT      360

TTAAGGNCTT TAAAAATGTT ANNTTTTCCC NTGCCNGGGT TAAAAAAGGA AAAAACTNAA      420

AAA                                                                   423

(2) INFORMATION FOR SEQ ID NO: 62:

(i) SEQUENCE CHARACTERISTICS:
        (A) LENGTH: 683 base pairs
        (B) TYPE: nucleic acid
        (C) STRANDEDNESS: single
        (D) TOPOLOGY: linear (xi) SEQUENCE DESCRIPTION: SEQ ID NO: 62:

GCTGGAGAGG GGTACGGACT TTCTTGGAGT TGTCCCAGGT TGGAATGAGA CTGAACTCAA       60

GAAGAGACCC TAAGAGACTG GGGAATGGTT CCTGCCTTCA GGAAAGTGAA AGACGCTTAG      120

GCTGTCAACA CTTAAAGGAA GTCCCCTTGA AGCCCAGAGT GGACAGACTA GACCCATTGA      180

TGGGGCCACT GGCCATGGTC CGTGGACAAG ACATTCCNGT GGGCCATGGC ACACCGGGGG      240

GGATCAAAAT GTGTACTTGT GGGGTCTCGC CCCTTGCCAA AACCAAACCA NTCCCACTCC      300

TGTCNTTGGA CTTTCTTCCC ATTCCCTCCT CCCCAAATGC ACTTCCCCTC CTCCCTCTGC      360

CCCTCCTGTG TTTTTGGAAT TCTGTTTCCC TCAAAATTGT TAATTTTTTA NTTTTNGACC      420

ATGAACTTAT GTTTGGGGTC NANGTTCCCC TTNCCAATGC ATACTAATAT ATTAATGGTT      480

ATTTATTTTT GAAATATTTT TTAATGAACT TGGAAAAAAT TNNTGGAATT TCCTTNCTTC      540

CNTTTTNTTT GGGGGGGGTG GGGGGNTGGG TTAAAATTTT TTTGGAANCC CNATNGGAAA      600

TTNTTACTTG GGGCCCCCCT NAAAAAANTN ANTTCCAATT CTTNNATNGC CCCTNTTCCN      660

CTAAAAAAAA ANANANNAAA AAN                                             683

(2) INFORMATION FOR SEQ ID NO: 63:

(i) SEQUENCE CHARACTERISTICS:
        (A) LENGTH: 731 base pairs
        (B) TYPE: nucleic acid
        (C) STRANDEDNESS: single
        (D) TOPOLOGY: linear (xi) SEQUENCE DESCRIPTION: SEQ ID NO: 63:

ACTAGTCATA AAGGGTGTGC GCGTCTTCGA CGTGGCGGTC TTGGCGCCAC TGCTGCGAGA       60

CCCGGCCCTG GACCTCAAGG TCATCCACTT GGTGCGTGAT CCCCGCGCGG TGGCGAGTTC      120

ACGGATCCGC TCGCGCCACG GCCTCATCCG TGAGAGCCTA CAGGTGGTGC GCAGCCGAGA      180

CCGCGAGCTC ACCGCATGCC CTTCTTGGAG GCCGCGGGCC ACAAGCTTGG CGCCCANAAA      240

GAAGGCGTNG GGGGCCCGCA AANTACCACG CTCTGGGCGC TATGGAANGT CCTCTTGCAA      300

TAATATTGGT TNAAAANCTG CANAANAGCC CCTGCANCCC CCTGAACTGG GNTGCAGGGC      360

CNCTTACCTN GTTTGGNTGC GGTTACAAAG AACCTGTTTN GGAAAACCCT NCCNAAAACC      420

TTCCGGGAAA ATTNTNCAAA TTTTTNTTGG GGAATTNTTG GGTAAACCCC CCNAAAATGG      480

GAAACNTTTT TGCCCTNNAA ANTAAACCAT TNGGTTCCGG GGGCCCCCCC NCAAAACCCT      540

TTTTTNTTTT TTTNTGCCCC CANTNNCCCC CCGGGGCCCC TTTTTTTGG GGAAAANCCC      600

CCCCCCTNCC NANANTTTTA AAAGGGNGGG ANAATTTTTN NTTNCCCCCC GGGNCCCCCN      660

GGNGNTAAAA NGGTTTCNCC CCCCCGAGGG GNGGGGNNNC CTCNNAAACC CNTNTCNNNA      720
```

CCNCNTTTTN N 731

(2) INFORMATION FOR SEQ ID NO: 64:

(i) SEQUENCE CHARACTERISTICS:
        (A) LENGTH: 313 base pairs
        (B) TYPE: nucleic acid
        (C) STRANDEDNESS: single
        (D) TOPOLOGY: linear (xi) SEQUENCE DESCRIPTION: SEQ ID NO: 64:

ACTAGTTGTG CAAACCACGA CTGAAGAAAG ACGAAAAGTG GGAAATAACT TGCAACGTCT 60

GTTAGAGATG GTTGCTACAC ATGTTGGGTC TGTAGAGAAA CATCTTGAGG AGCAGATTGC 120

TAAAGTTGAT AGAGAATATG AAGAATGCAT GTCAGAAGAT CTCTCGGAAA ATATTAAAGA 180

GATTAGAGAT AAGTATGAGA AGAAAGCTAC TCTAATTAAG TCTTCTGAAG AATGAAGATN 240

AAATGTTGAT CATGTATATA TATCCATAGT GAATAAAATT GTCTCAGTAA AGTTGTAAAA 300

AAAAAAAAAA AAA 313

(2) INFORMATION FOR SEQ ID NO: 65:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (xi) SEQUENCE DESCRIPTION: SEQ ID NO: 65:

ACTAGTTCCC TGGCAGGCAA GGGCTTCCAA CTGAGGCAGT GCATGTGTGG CAGAGAGAGG 60

CAGGAAGCTG GCAGTGGCAG CTTCTGTGTC TAGGGAGGGG TGTGGCTCCC TCCTTCCCTG 120

TCTGGGAGGT TGGAGGGAAG AATCTAGGCC TTAGCTTGCC CTCCTGCCAC CCTTCCCCTT 180

GTAGATACTG CCTTAACACT CCCTCCTCTC TCAGCTGTGG CTGCCACCCA AGCCAGGTTT 240

CTCCGTGCTC ACTAATTTAT TTCCAGGAAA GGTGTGTGGA AGACATGAGC CGTGTATAAT 300

ATTTGTTTTA ACATTTTCAT TGCAAGTATT GACCATCATC CTTGGTTGTG TATCGTTGTA 360

ACACAAATTA ATGATATTAA AAAGCATCCA AACAAAGCCN ANNNNNAANA NNANNNGAAA 420

(2) INFORMATION FOR SEQ ID NO: 66:

(i) SEQUENCE CHARACTERISTICS:
        (A) LENGTH: 676 base pairs
        (B) TYPE: nucleic acid
        (C) STRANDEDNESS: single
        (D) TOPOLOGY: linear (xi) SEQUENCE DESCRIPTION: SEQ ID NO: 66:

ACTAGTTTCC TATGATCATT AAACTCATTC TCAGGGTTAA GAAAGGAATG TAAATTTCTG 60

CCTCAATTTG TACTTCATCA ATAAGTTTTT GAAGAGTGCA GATTTTTAGT CAGGTCTTAA 120

AAATAAACTC ACAAATCTGG ATGCATTTCT AAATTCTGCA AATGTTTCCT GGGGTGACTT 180

AACAAGGAAT AATCCCACAA TATACCTAGC TACCTAATAC ATGGAGCTGG GGCTCAACCC 240

ACTGTTTTTA AGGATTTGCG CTTACTTGTG GCTGAGGAAA AATAAGTAGT TCCGAGGGAA 300

GTAGTTTTTA AATGTGAGCT TATAGATNGG AAACAGAATA TCAACTTAAT TATGGAAATT 360

GTTAGAAACC TGTTCTCTTG TTATCTGAAT CTTGATTGCA ATTACTATTG TACTGGATAG 420

ACTCCAGCCC ATTGCAAAGT CTCAGATATC TTANCTGTGT AGTTGAATTC CTTGGAAATT 480

CTTTTTAAGA AAAAATTGGA GTTTNAAAGA AATAAACCCC TTTGTTAAAT GAAGCTTGGC 540

```
TTTTTGGTGA AAAANAATCA TCCCGCAGGG CTTATTGTTT AAAAANGGAA TTTTAAGCCT      600

CCCTGGAAAA ANTTGTTAAT TAAATGGGGA AAATGNTGGG NAAAAATTAT CCGTTAGGGT      660

TTAAAGGGAA AACTTA                                                     676
```

(2) INFORMATION FOR SEQ ID NO: 67:

(i) SEQUENCE CHARACTERISTICS:
        (A) LENGTH: 620 base pairs
        (B) TYPE: nucleic acid
        (C) STRANDEDNESS: single
        (D) TOPOLOGY: linear (xi) SEQUENCE DESCRIPTION: SEQ ID NO: 67:

```
CACCATTAAA GCTGCTTACC AAGAACTTCC CCAGCATTTT GACTTCCTTG TTTGATAGCT       60

GAATTGTGAG CAGGTGATAG AAGAGCCTTT CTAGTTGAAC ATACAGATAA TTTGCTGAAT      120

ACATTCCATT TAATGAAGGG GTTACATCTG TTACGAAGCT ACTAAGAAGG AGCAAGAGCA      180

TAGGGGAAAA AAATCTGATC AGAACGCATC AAACTCACAT GTGCCCCCTC TACTACAAAC      240

AGATTGTAGT GCTGTGGTGG TTTATTCCGT TGTGCAGAAC TTGCAAGCTG AGTCACTAAA      300

CCCAAAGAGA GGAAATTATA GGTTAGTTAA ACATTGTAAT CCCAGGAACT AAGTTTAATT      360

CACTTTTGAA GTGTTTTGTT TTTTATTTTT GGTTTGTCTG ATTTACTTTG GGGGAAAANG      420

CTAAAAAAAA AGGGATATCA ATCTCTAATT CAGTGCCCAC TAAAAGTTGT CCCTAAAAAG      480

TCTTTACTGG AANTTATGGG ACTTTTTAAG CTCCAGGTNT TTTGGTCCTC CAAATTAACC      540

TTGCATGGGC CCCTTAAAAT TGTTGAANGG CATTCCTGCC TCTAAGTTTG GGGAAAATTC      600

CCCCNTTTTN AAAATTTGGA                                                 620
```

(2) INFORMATION FOR SEQ ID NO: 68:

(i) SEQUENCE CHARACTERISTICS:
        (A) LENGTH: 551 base pairs
        (B) TYPE: nucleic acid
        (C) STRANDEDNESS: single
        (D) TOPOLOGY: linear (xi) SEQUENCE DESCRIPTION: SEQ ID NO: 68:

```
ACTAGTAGCT GGTACATAAT CACTGAGGAG CTATTTCTTA ACATGCTTTT ATAGACCATG       60

CTAATGCTAG ACCAGTATTT AAGGGCTAAT CTCACACCTC CTTAGCTGTA AGAGTCTGGC      120

TTAGAACAGA CCTCTCTGTG CAATAACTTG TGGCCACTGG AAATCCCTGG GCCGGCATTT      180

GTATTGGGGT TGCAATGACT CCCAAGGGCC AAAAGAGTTA AAGGCACGAC TGGGATTTCT      240

TCTGAGACTG TGGTGAAACT CCTTCCAAGG CTGAGGGGGT CAGTANGTGC TCTGGGAGGG      300

ACTCGGCACC ACTTTGATAT TCAACAAGCC ACTTGAAGCC CAATTATAAA ATTGTTATTT      360

TACAGCTGAT GGAACTCAAT TTGAACCTTC AAAACTTTGT TAGTTTATCC TATTATATTG      420

TTAAACCTAA TTACATTTGT CTAGCATTGG ATTTGGTTCC TGTNGCATAT GTTTTTTTCN      480

CCTATGTGCT CCCCTCCCCC NNATCTTAAT TTAAACCNCA ATTTTGCNAT TCNCCNNNNN      540

NANNNANNNA A                                                          551
```

(2) INFORMATION FOR SEQ ID NO: 69:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (xi) SEQUENCE DESCRIPTION: SEQ ID NO: 69:

```
CAGAAATGGA AAGCAGAGTT TTCATTTCTG TTTATAAACG TCTCCAAACA AAAATGGAAA    60
GCAGAGTTTT CATTAAATCC TTTTACCTTT TTTTTTTCTT GGTAATCCCC TCAAATAACA   120
GTATGTGGGA TATTGAATGT TAAAGGGATA TTTTTTTCTA TTATTTTTAT AATTGTACAA   180
AATTAAGCAA ATGTTAAAAG TTTTATATGC TTTATTAATG TTTTCAAAAG GTATNATACA   240
TGTGATACAT TTTTTAAGCT TCAGTTGCTT GTCTTCTGGT ACTTTCTGTT ATGGGCTTTT   300
GGGGAGCCAN AAACCAATCT ACNATCTCTT TTTGTTTGCC AGGACATGCA ATAAAATTTA   360
AAAAATAAAT AAAAACTATT NAGAAATTGA AAAAAA                             396
```

(2) INFORMATION FOR SEQ ID NO: 70:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 70:

```
ACTAGTGCAA AAGCAAATAT AAACATCGAA AAGGCGTTCC TCACGTTAGC TGAAGATATC    60
CTTCGAAAGA CCCCTGTAAA AGAGCCCAAC AGTGAAAATG TAGATATCAG CAGTGGAGGA   120
GGCGTGACAG GCTGGAAGAG CAAATGCTGC TGAGCATTCT CCTGTTCCAT CAGTTGCCAT   180
CCACTACCCC GTTTTCTCTT CTTGCTGCAA AATAAACCAC TCTGTCCATT TTTAACTCTA   240
AACAGATATT TTTGTTTCTC ATCTTAACTA TCCAAGCCAC CTATTTTATT TGTTCTTTCA   300
TCTGTGACTG CTTGCTGACT TTATCATAAT TTTCTTCAAA CAAAAAAATG TATAGAAAAA   360
TCATGTCTGT GACTTCATTT TTAAATGNTA CTTGCTCAGC TCAACTGCAT TTCAGTTGTT   420
TTATAGTCCA GTTCTTATCA ACATTNAAAC CTATNGCAAT CATTTCAAAT CTATTCTGCA   480
AATTGTATAA GAATAAAAGT TAGAATTTAA CAATTAAAAA AAAAAAAAA AAAAAA        536
```

(2) INFORMATION FOR SEQ ID NO: 71:

(i) SEQUENCE CHARACTERISTICS:
        (A) LENGTH: 865 base pairs
        (B) TYPE: nucleic acid
        (C) STRANDEDNESS: single
        (D) TOPOLOGY: linear (xi) SEQUENCE DESCRIPTION: SEQ ID NO: 71:

```
GACAAAGCGT TAGGAGAAGA ANAGAGGCAG GGAANACTNC CCAGGCACGA TGGCCNCCTT    60
CCCACCAGCA ACCAGCGCCC CCCACCAGCC CCCAGGCCCG GACGACGAAG ACTCCATCCT   120
GGATTAATCT NACCTCTNTC GCCTGNCCCA TTCCTACCTC GGAGGTGGAG GCCGGAAAGG   180
TCNCACCAAG AGANAANCTG CTGCCAACAC CAACCGCCCC AGCCCTGGCG GCACGANAG    240
GAAACTGGTG ACCAATCTGC AGAATTCTNA GAGGAANAAG CNAGGGGCCC CGCGCTNAGA   300
CAGAGCTGGA TATGANGCCA GACCATGGAC NCTACNCCCN NCAATNCANA CGGGACTGCG   360
GAAGATGGAN GACCCNCGAC NNGATCAGGC CNGCTNNCCA NCCCCCCACC CCTATGAATT   420
ATTCCCGCTG AANGAATCTC TGANNGGCTT CCANNAAAGC GCCTCCCCNC CNAACGNAAN   480
TNCAACATNG GGATTANANG CTGGGAACTG NAAGGGGCAA ANCCTNNAAT ATCCCCAGAA   540
ACAANCTCTC CCNAANAAAC TGGGGCNCCT CATNGGTGGN ACCAACTATT AACTAAACCG   600
```

| | |
|---|---|
| CACGCCAAGN AANTATAAAA GGGGGGCCCC TCCNCGGNNG ACCCCCTTTT GTCCCTTAAT | 660 |
| GANGGTTATC CNCCTTGCGT ACCATGGTNC CCNNTTCTGT NTGNATGTTT CCNCTCCCCT | 720 |
| CCNCCTATNT CNAGCCGAAC TCNNATTTNC CCGGGGGTGC NATCNANTNG TNCNCCTTTN | 780 |
| TTNGTTGNCC CNGCCCTTTC CGNCGGAACN CGTTTCCCCG TTANTAACGG CACCCGGGGN | 840 |
| AAGGGTGNTT GGCCCCCTCC CTCCC | 865 |

(2) INFORMATION FOR SEQ ID NO: 72:

(i) SEQUENCE CHARACTERISTICS:
        (A) LENGTH: 560 base pairs
        (B) TYPE: nucleic acid
        (C) STRANDEDNESS: single
        (D) TOPOLOGY: linear (xi) SEQUENCE DESCRIPTION: SEQ ID NO: 72:

| | |
|---|---|
| CCTGGACTTG TCTTGGTTCC AGAACCTGAC GACCCGGCGA CGGCGACGTC TCTTTTGACT | 60 |
| AAAAGACAGT GTCCAGTGCT CCNGCCTAGG AGTCTACGGG GACCGCCTCC CGCGCCGCCA | 120 |
| CCATGCCCAA CTTCTCTGGC AACTGGAAAA TCATCCGATC GGAAAACTTC GANGAATTGC | 180 |
| TCNAANTGCT GGGGGTGAAT GTGATGCTNA NGAANATTGC TGTGGCTGCA GCGTCCAAGC | 240 |
| CAGCAGTGGA GATCNAACAG GAGGGAGACA CTTTCTACAT CAAAACCTCC ACCACCGTGC | 300 |
| GCACCACAAA GATTAACTTC NNNGTTGGGG AGGANTTTGA GGANCAAACT GTGGATNGGA | 360 |
| NGCCTGTNAA AACCTGGTGA AATGGGAGAA TGANAATAAA ATGGTCTGTG ANCANAAACT | 420 |
| CCTGAAAGGA GAAGGCCCCC ANAACTCCTG GACCNGAAAA ACTGACCCNC CNATNGGGGA | 480 |
| ACTGATNCTT GAACCCTGAA CGGGCGGGAT GANCCTTTTT TNTTGCCNCC NAANGGGTTC | 540 |
| TTTCCNTTTC CCCAAAAAAA | 560 |

(2) INFORMATION FOR SEQ ID NO: 73:

(i) SEQUENCE CHARACTERISTICS:
        (A) LENGTH: 379 base pairs
        (B) TYPE: nucleic acid
        (C) STRANDEDNESS: single
        (D) TOPOLOGY: linear (xi) SEQUENCE DESCRIPTION: SEQ ID NO: 73:

| | |
|---|---|
| CTGGGGANCC GGCGGTNNGC NCCATNTCNN GNCGCGAAGG TGGCAATAAA AANCCNCTGA | 60 |
| AACCGCNCAA NAAACATGCC NAAGATATGG ACGAGGAAGA TNGNGCTTTC NNGNACAANC | 120 |
| GNANNGAGGA ACANAACAAA CTCNANGAGC TCTCAAGCTA ATGCCGCGGG GAAGGGGCCC | 180 |
| TTGGCCACNN GTGGAATTAA GAAATCTGGC AAANNGTANN TGTTCCTTGT GCCTNANGAG | 240 |
| ATAAGNGACC CTTTATTTCA TCTGTATTTA AACCTCTCTN TTCCCTGNCA TAACTTCTTT | 300 |
| TNCCACGTAN AGNTGGAANT ANTTGTTGTC TTGGACTGTT GTNCATTTTA GANNAAACTT | 360 |
| TTGTTCAAAA AAAAAATAA | 379 |

(2) INFORMATION FOR SEQ ID NO: 74:

(i) SEQUENCE CHARACTERISTICS:
        (A) LENGTH: 437 base pairs
        (B) TYPE: nucleic acid
        (C) STRANDEDNESS: single
        (D) TOPOLOGY: linear (xi) SEQUENCE DESCRIPTION: SEQ ID NO: 74:

| | |
|---|---|
| ACTAGTTCAG ACTGCCACGC CAACCCCAGA AAATACCCCA CATGCCAGAA AAGTGAAGTC | 60 |

```
CTAGGTGTTT CCATCTATGT TTCAATCTGT CCATCTACCA GGCCTCGCGA TAAAAACAAA        120

ACAAAAAAAC GCTGCCAGGT TTTANAAGCA GTTCTGGTCT CAAAACCATC AGGATCCTGC        180

CACCAGGGTT CTTTTGAAAT AGTACCACAT GTAAAAGGGA ATTTGGCTTT CACTTCATCT        240

AATCACTGAA TTGTCAGGCT TGATTGATA ATTGTAGAAA TAAGTAGCCT TCTGTTGTGG         300

GAATAAGTTA TAATCAGTAT TCATCTCTTT GTTTTTTGTC ACTCTTTTCT CTCTNATTGT        360

GTCATTTGTA CTGTTTGAAA AATATTTCTT CTATAAAATT AAACTAACCT GCCTTAAAAA        420

AAAAAAAAAA AAAAAAA                                                      437
```

(2) INFORMATION FOR SEQ ID NO: 75:

(i) SEQUENCE CHARACTERISTICS:
        (A) LENGTH: 579 base pairs
        (B) TYPE: nucleic acid
        (C) STRANDEDNESS: single
        (D) TOPOLOGY: linear (xi) SEQUENCE DESCRIPTION: SEQ ID NO: 75:

```
CTCCGTCGCC GCCAAGATGA TGTGCGGGGC GCCCTCCGCC ACGCAGCCGG CCACCGCCGA         60

GACCCAGCAC ATCGCCGACC AGGTGAGGTC CCAGCTTGAA GAGAAAGAAA ACAAGAAGTT        120

CCCTGTGTTT AAGGCCGTGT CATTCAAGAG CCAGGTGGTC GCGGGACAA ACTACTTCAT         180

CAAGGTGCAC GTCGGCGACG AGGACTTCGT ACACCTGCGA GTGTTCCAAT CTCTCCCTCA        240

TGAAAACAAG CCCTTGACCT TATCTAACTA CCAGACCAAC AAAGCCAAGC ATGATGAGCT        300

GACCTATTTC TGATCCTGAC TTTGGACAAG GCCCTTCAGC CAGAAGACTG ACAAAGTCAT        360

CCTCCGTCTA CCAGAGCGTG CACTTGTGAT CCTAAAATAA GCTTCATCTC CGGGCTGTGC        420

CCTTGGGGTG GAAGGGGCAN GATCTGCACT GCTTTTGCAT TTCTCTTCCT AAATTTCATT        480

GTGTTGATTC TTTCCTTCCA ATAGGTGATC TTNATTACTT TCAGAATATT TTCCAAATNA        540

GATATATTTT NAAAATCCTT AAAAAAAAAA AAAAAAAA                                579
```

(2) INFORMATION FOR SEQ ID NO: 76:

(i) SEQUENCE CHARACTERISTICS:
        (A) LENGTH: 666 base pairs
        (B) TYPE: nucleic acid
        (C) STRANDEDNESS: single
        (D) TOPOLOGY: linear (xi) SEQUENCE DESCRIPTION: SEQ ID NO: 76:

```
GTTTATCCTA TCTCTCCAAC CAGATTGTCA GCTCCTTGAG GGCAAGAGCC ACAGTATATT         60

TCCCTGTTTC TTCCACAGTG CCTAATAATA CTGTGGAACT AGGTTTTAAT AATTTTTTAA        120

TTGATGTTGT TATGGGCAGG ATGGCAACCA GACCATTGTC TCAGAGCAGG TGCTGGCTCT        180

TTCCTGGCTA CTCCATGTTG GCTAGCCTCT GGTAACCTCT TACTTATTAT CTTCAGGACA        240

CTCACTACAG GGACCAGGGA TGATGCAACA TCCTTGTCTT TTTATGACAG GATGTTTGCT        300

CAGCTTCTCC AACAATAAAA AGCACGTGGT AAAACACTTG CGGATATTCT GGACTGTTTT        360

TAAAAAATAT ACAGTTTACC GAAAATCATA TTATCTTACA ATGAAAAGGA NTTTATAGAT        420

CAGCCAGTGA ACAACCTTTT CCACCATAC AAAAATTCCT TTTCCCGAAN GAAAANGGCT         480

TTCTCAATAA NCCTCACTTT CTTAANATCT TACAAGATAG CCCCGANATC TTATCGAAAC        540

TCATTTTAGG CAAATATGAN TTTTATTGTN CGTTACTTGT TTCAAAATTT GGTATTGTGA        600

ATATCAATTA CCACCCCCAT CTCCCATGAA ANAAANGGGA AANGGTGAAN TTCNTAANCG        660

CTTAAA                                                                  666
```

(2) INFORMATION FOR SEQ ID NO: 77:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (xi) SEQUENCE DESCRIPTION: SEQ ID NO: 77:

```
CTGCAGCCCG GGGGATCCAC TAATCTACCA NGGTTATTTG GCAGCTAATT CTANATTTGG      60

ATCATTGCCC AAAGTTGCAC TTGCTGGTCT CTTGGGATTT GGCCTTGGAA AGGTATCATA     120

CATANGANTA TGCCANAATA AATTCCATTT TTTTGAAAAT CANCTCCNTG GGGCTGGTTT     180

TGGTCCACAG CATAACANGC ACTGCCTCCT TACCTGTGAG GAATGCAAAA TAAAGCATGG    240

ATTAAGTGAG AAGGGAGACT CTCAGCCTTC AGCTTCCTAA ATTCTGTGTC TGTGACTTTC    300

GAAGTTTTTT AAACCTCTGA ATTTGTACAC ATTTAAAATT TCAAGTGTAC TTTAAAATAA    360

AATACTTCTA ATGGGAACAA AAAAAAAAAA AAAAAA                              396
```

(2) INFORMATION FOR SEQ ID NO: 78:

(i) SEQUENCE CHARACTERISTICS:
        (A) LENGTH: 793 base pairs
        (B) TYPE: nucleic acid
        (C) STRANDEDNESS: single
        (D) TOPOLOGY: linear (xi) SEQUENCE DESCRIPTION: SEQ ID NO: 78:

```
GCATCCTAGC CGCCGACTCA CACAAGGCAG GTGGGTGAGG AAATCCAGAG TTGCCATGGA      60

GAAAATTCCA GTGTCAGCAT TCTTGCTCCT TGTGGCCCTC TCCTACACTC TGGCCAGAGA    120

TACCACAGTC AAACCTGGAG CCAAAAAGGA CACAAAGGAC TCTCGACCCA AACTGCCCCA    180

GACCCTCTCC AGAGGTTGGG GTGACCAACT CATCTGGACT CAGACATATG AAGAAGCTCT    240

ATATAAATCC AAGACAAGCA ACAAACCCTT GATGATTATT CATCACTTGG ATGAGTGCCC    300

ACACAGTCNA GCTTTAAAGA AAGTGTTTGC TGAAAATAAA GAAATCCAGA AATTGGCAGA    360

GCAGTTTGTC CTCCTCAATC TGGTTTATGA ACAACTGAC AAACACCTTT CTCCTGATGG     420

CCAGTATGTC CCAGGATTAT GTTTGTTGAC CCATCTCTGA CAGTTGAAGC CGATATCCTG    480

GGAAGATATT CNAACCGTCT CTATGCTTAC AAACTGCAGA TACGCTCTGT TGCTTGACAC    540

ATGAAAAAGC TCTCAAGTTG CTNAAAATGA ATTGTAAGAA AAAAAATCTC CAGCCTTCTG    600

TCTGTCGGCT TGAAAATTGA ACCAGAAAA ATGTGAAAAA TGGCTATTGT GGAACANATN     660

GACACCTGAT TAGGTTTTGG TTATGTTCAC CACTATTTTT AANAAAANAN NTTTTAAAAT    720

TTGGTTCAAT TNTCTTTTTN AAACAATNTG TTTCTACNTT GNGANCTGAT TTCTAAAAAA    780

AATAATNTTT GGC                                                        793
```

(2) INFORMATION FOR SEQ ID NO: 79:

(i) SEQUENCE CHARACTERISTICS:
        (A) LENGTH: 456 base pairs
        (B) TYPE: nucleic acid
        (C) STRANDEDNESS: single
        (D) TOPOLOGY: linear (xi) SEQUENCE DESCRIPTION: SEQ ID NO: 79:

```
ACTAGTATGG GGTGGGAGGC CCCACCCTTC TCCCCTAGGC GCTGTTCTTG CTCCAAAGGG      60

CTCCGTGGAG AGGGACTGGC AGAGCTGANG CCACCTGGGG CTGGGGATCC CACTCTTCTT    120
```

-continued

```
GCAGCTGTTG AGCGCACCTA ACCACTGGTC ATGCCCCCAC CCCTGCTCTC CGCACCCGCT      180

TCCTCCCGAC CCCANGACCA GGCTACTTCT CCCCTCCTCT TGCCTCCCTC CTGCCCCTGC      240

TGCCTCTGAT CGTANGAATT GANGANTGTC CCGCCTTGTG GCTGANAATG GACAGTGGCA      300

GGGGCTGGAA ATGGGTGTGT GTGTGTGTGT GTGTGTGTGT GTGTGTGTGT GCNCCCCCCC      360

TGCAAGACCG AGATTGAGGG AAANCATGTC TGCTGGGTGA GACCATGTTT CCTCTCCATA      420

AANTNCCCCT GTGACNCTCA NAAAAAAAAA AAAAAA                                456
```

(2) INFORMATION FOR SEQ ID NO: 80:

(i) SEQUENCE CHARACTERISTICS:
        (A) LENGTH: 284 base pairs
        (B) TYPE: nucleic acid
        (C) STRANDEDNESS: single
        (D) TOPOLOGY: linear (xi) SEQUENCE DESCRIPTION: SEQ ID NO: 80:

```
CTTTGTACCT CTAGAAAAGA TAGGTATTGT GTCATGAAAC TTGAGTTTAA ATTTTATATA       60

TAAAACTAAA AGTAATGCTC ACTTTAGCAA CACATACTAA AATTGGAACC ATACTGAGAA      120

GAATAGCATG ACCTCCGTGC AAACAGGACA AGCAAATTTG TGATGTGTTG ATTAAAAAGA      180

AATAAATAAA TGTGTATATG TGTAACTTGT ATGTTTATGT GGAATACAGA TTGGGAAATA      240

AAATGTATTT CTTACTGTGA AAAAAAAAAA AAAAAAAAAA AANA                      284
```

(2) INFORMATION FOR SEQ ID NO: 81:

(i) SEQUENCE CHARACTERISTICS:
        (A) LENGTH: 671 base pairs
        (B) TYPE: nucleic acid
        (C) STRANDEDNESS: single
        (D) TOPOLOGY: linear (xi) SEQUENCE DESCRIPTION: SEQ ID NO: 81:

```
GCCACCAACA TTCCAAGCTA CCCTGGGTAC CTTTGTGCAG TAGAAGCTAG TGAGCATGTG       60

AGCAAGCGGT GTGCACACGG AGACTCATCG TTATAATTTA CTATCTGCCA AGAGTAGAAA      120

GAAAGGCTGG GGATATTTGG GTTGGCTTGG TTTTGATTTT TTGCTTGTTT GTTTGTTTTG      180

TACTAAAACA GTATTATCTT TTGAATATCG TAGGGACATA AGTATATACA TGTTATCCAA      240

TCAAGATGGC TAGAATGGTG CCTTTCTGAG TGTCTAAAAC TTGACACCCC TGGTAAATCT      300

TTCAACACAC TTCCACTGCC TGCGTAATGA AGTTTTGATT CATTTTTAAC CACTGGAATT      360

TTTCAATGCC GTCATTTTCA GTTAGATNAT TTTGCACTTT GAGATTAAAA TGCCATGTCT      420

ATTTGATTAG TCTTATTTTT TTATTTTTAC AGGCTTATCA GTCTCACTGT TGGCTGTCAT      480

TGTGACAAAG TCAAATAAAC CCCCNAGGAC AACACACAGT ATGGGATCAC ATATTGTTTG      540

ACATTAAGCT TTGGCCAAAA AATGTTGCAT GTGTTTTACC TCGACTTGCT AAATCAATAN      600

CANAAAGGCT GGCTNATAAT GTTGGTGGTG AAATAATTAA TNANTAACCA AAAAAAAAN      660

AAAAAAAAA A                                                            671
```

(2) INFORMATION FOR SEQ ID NO: 82:

(i) SEQUENCE CHARACTERISTICS:
        (A) LENGTH: 217 base pairs
        (B) TYPE: nucleic acid
        (C) STRANDEDNESS: single
        (D) TOPOLOGY: linear (xi) SEQUENCE DESCRIPTION: SEQ ID NO: 82:

CTGCAGATGT TTCTTGAATG CTTTGTCAAA TTAANAAAGT TAAAGTGCAA TAATGTTTGA    60

AGACAATAAG TGGTGGTGTA TCTTGTTTCT AATAAGATAA ACTTTTTTGT CTTTGCTTTA   120

TCTTATTAGG GAGTTGTATG TCAGTGTATA AAACATACTG TGTGGTATAA CAGGCTTAAT   180

AAATTCTTTA AAAGGAAAAA AAAAAAAAAA AAAAAA                              217

(2) INFORMATION FOR SEQ ID NO: 83:

(i) SEQUENCE CHARACTERISTICS:
        (A) LENGTH: 460 base pairs
        (B) TYPE: nucleic acid
        (C) STRANDEDNESS: single
        (D) TOPOLOGY: linear (xi) SEQUENCE DESCRIPTION: SEQ ID NO: 83:

CGCGAGTGGG AGCACCAGGA TCTCGGGCTC GGAACGAGAC TGCACGGATT GTTTTAAGAA    60

AATGGCAGAC AAACCAGACA TGGGGGAAAT CGCCAGCTTC GATNAGGCCA AGCTGAANAA   120

AACGGAGACG CAGGAGAAGA ACACCCTGCC GACCAAAGAG ACCATTGAGC ANGAGAAGCG   180

GAGTGAAATT TCCTAAGATC CTGGAGGATT TCCTACCCCC GTCCTCTTCG AGACCCCAGT   240

CGTGATGTGG AGGAAGAGCC ACCTGCAAGA TGGACACGAG CCACAAGCTG CACTGTGAAC   300

CTGGGCACTC CGCGCCGATG CCACCGGCCT GTGGGTCTCT GAAGGGACCC CCCCCAATCG   360

GACTGCCAAA TTCTCCGGTT TGCCCCGGGA TATTATACAA NATTATTTGT ATGAATAATG   420

ANNATAAAAC ACACCTCGTG GCANCAAANA AAAAAAAAA                           460

(2) INFORMATION FOR SEQ ID NO: 84:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (xi) SEQUENCE DESCRIPTION: SEQ ID NO: 84:

TGGTGGATCT TGGCTCTGTG GAGCTGCTGG GACGGGATCT AAAAGACTAT TCTGGAAGCT    60

GTGGTCCAAN GCATTTTGCT GGCTTAACGG GTCCCGGAAC AAAGGACACC AGCTCTCTAA   120

AATTGAAGTT TACCCGANAT AACAATCTTT TGGGCAGAGA TGCCTATTTT AACAAACNCC   180

GTCCCTGCGC AACAACNAAC AATCTCTGGG AAATACCGGC CATGAACNTG CTGTCTCAAT   240

CNANCATCTC TCTAGCTGAC CGATCATATC GTCCCAGATT ACTACANATC ATAATAATTG   300

ATTTCCTGTA NAAAAAAAA AAA                                             323

(2) INFORMATION FOR SEQ ID NO: 85:

(i) SEQUENCE CHARACTERISTICS:
        (A) LENGTH: 771 base pairs
        (B) TYPE: nucleic acid
        (C) STRANDEDNESS: single
        (D) TOPOLOGY: linear (xi) SEQUENCE DESCRIPTION: SEQ ID NO: 85:

AAACTGGGTA CTCAACACTG AGCAGATCTG TTCTTTGAGC TAAAAACCAT GTGCTGTACC    60

AANAGTTTGC TCCTGGCTGC TTTGATGTCA GTGCTGCTAC TCCACCTCTG CGGCGAATCA   120

GAAGCAAGCA ACTTTGACTG CTGTCTTGGA TACACAGACC GTATTCTTCA TCCTAAATTT   180

ATTGTGGGCT TCACACGGCA GCTGGCCAAT GAAGGCTGTG ACATCAATGC TATCATCTTT   240

CACACAAAGA AAAAGTTGTC TGTGTGCGCA AATCCAAAAC AGACTTGGGT GAAATATATT   300

```
GTGCGTCTCC TCAGTAAAAA AGTCAAGAAC ATGTAAAAAC TGTGGCTTTT CTGGAATGGA      360

ATTGGACATA GCCCAAGAAC AGAAAGAACT TGCTGGGGTT GGAGGTTTCA CTTGCACATC      420

ATGGANGGTT TAGTGCTTAT CTTATTTGTG CCTCCTGGAC TTGTCCAATT NATGAAGTTA      480

ATCATATTGC ATCATANTTT GCTTTGTTTA ACATCACATT NAAATTAAAC TGTATTTTAT      540

GTTATTTATA GCTNTAGGTT TTCTGTGTTT AACTTTTTAT ACNAANTTTC CTAAACTATT      600

TTGGTNTANT GCAANTTAAA AATTATATTT GGGGGGGGAA TAAATATTGG ANTTTCTGCA      660

GCCACAAGCT TTTTTTAAAA AACCANTACA NCCNNGTTAA ATGGTNGGTC CCNAATGGTT      720

TTTGCTTTTN ANTAGAAAAT TTNTTAGAAC NATTTGAAAA AAAAAAAAAA A              771

(2) INFORMATION FOR SEQ ID NO: 86:

(i) SEQUENCE CHARACTERISTICS:
        (A) LENGTH: 628 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 86:

ACTAGTTTGC TTTACATTTT TGAAAAGTAT TATTTTTGTC CAAGTGCTTA TCAACTAAAC       60

CTTGTGTTAG GTAAGAATGG AATTTATTAA GTGAATCAGT GTGACCCTTC TTGTCATAAG      120

ATTATCTTAA AGCTGAAGCC AAAATATGCT TCAAAAGAAA ANGACTTTAT TGTTCATTGT      180

AGTTCATACA TTCAAAGCAT CTGAACTGTA GTTTCTATAG CAAGCCAATT ACATCCATAA      240

GTGGAGAANG AAATAGATTA ATGTCNAAGT ATGATTGGTG GAGGGAGCAA GGTTGAAGAT      300

AATCTGGGGT TGAAATTTTC TAGTTTTCAT TCTGTACATT TTTAGTTNGA CATCAGATTT      360

GAAATATTAA TGTTTACCTT TCAATGTGTG GTATCAGCTG GACTCANTAA CACCCCTTTC      420

TTCCCTNGGG GATGGGGAAT GGATTATTGG AAAATGGAAA GAAAAAGTA CTTAAAGCCT       480

TCCTTTCNCA GTTTCTGGCT CCTACCCTAC TGATTTANCC AGAATAAGAA AACATTTTAT      540

CATCNTCTGC TTTATTCCCA TTAATNAANT TTTGATGAAT AAATCTGCTT TTATGCNNAC      600

CCAAGGAATT NAGTGGNTTC NTCNTTGT                                         628
```